(12) United States Patent
Matthews et al.

(10) Patent No.: US 7,763,605 B2
(45) Date of Patent: Jul. 27, 2010

(54) [1,4]BENZODIAZEPINES AS VASOPRESSIN V2 RECEPTOR ANTAGONISTS

(75) Inventors: Jay Matthews, Lansdale, PA (US); Bruce Maryanoff, New Hope, PA (US)

(73) Assignee: Janssen Pharmaceutica, N.V. (BE)

( * ) Notice: Subject to any disclaimer, the term of this patent is extended or adjusted under 35 U.S.C. 154(b) by 969 days.

(21) Appl. No.: 11/260,118

(22) Filed: Oct. 27, 2005

(65) Prior Publication Data

US 2006/0116367 A1 Jun. 1, 2006

Related U.S. Application Data

(60) Provisional application No. 60/623,053, filed on Oct. 28, 2004.

(51) Int. Cl.
- *A61P 9/00* (2006.01)
- *A61K 31/55* (2006.01)
- *C07D 243/14* (2006.01)

(52) U.S. Cl. ........................ 514/221; 540/573
(58) Field of Classification Search ............... 514/221; 540/573
See application file for complete search history.

(56) References Cited

U.S. PATENT DOCUMENTS 5,985,869 A * 11/1999 Ogawa et al. ............... 514/221

FOREIGN PATENT DOCUMENTS

WO  00/43398  7/2000
WO  03/037901  5/2003

OTHER PUBLICATIONS

Matthews, J. et al., "Potent nonpeptide vasopressin receptor antagonists based on oxazino-and thiazinobenzodiazepine templates" Bioorganic & Medicinal Chemistry Letters, Pergamon, Elsevier Science GB, vol. 14, No. 11; 2004 pp. 2747-2752.

Matsuhisa, et al., "Nonpeptide arginine vasopressin antagonists for both V1a and V2 receptors: synthesis and pharmacological properties of 2-phenyl-4-(2,3,4,5-tetrahydro-1H-1,5-benzodiazepine-1-carbonyl)benz anilide derivatives", Chemical and Pharmaceutical Bulletin Pharmaceutical society of Japan, Tokyo, vol. 46, No. 10, 1998 pp. 1566-1579.

Ogawa, et al., "Orally Active, Nonpeptide Vasopressin V2 receptor Antagonists", Journal of Medicinal Chemistry, US American Chemical Society. Washington, vol. 39, No. 18 1996 pp. 3547-3555.

Ohtake, et al., Novel Vasopressin V2 Receptor-selective Antagonists Pyrrolo[2,1-a]quinoxaline and Pyrrolo[2,1-c][1,4]benzodiazepine Derivatives Bioorganic & Medicinal Chemistry, Elsevier Science Ltd, GB, vol. 7, No. 6, 1999 pp. 1247-1254.

Fujisawa, et al., "Therapeutic efficacy of non-peptide ADH antagonist OPC-31260 in SIADH rats", Kidney International, vol. 44, 1993 pp. 19-23.

* cited by examiner

*Primary Examiner*—Brenda L Coleman
(74) *Attorney, Agent, or Firm*—Yuriy P. Stercho

(57) ABSTRACT

The invention is directed to novel [1,4]benzodiazepine compounds useful as vasopressin receptor antagonists for treating conditions involving increased vascular resistance and cardiac insufficiency. Pharmaceutical compositions comprising [1,4]benzodiazepine compounds of the present invention and methods of treating conditions such as hypertension, congestive heart failure, cardiac insufficiency, coronary vasospasm, cardiac ischemia, liver cirrhosis, renal vasospasm, renal failure, cerebral edema and ischemia, stroke, thrombosis, or water retention are also disclosed.

40 Claims, No Drawings

[1,4]BENZODIAZEPINES AS VASOPRESSIN V2 RECEPTOR ANTAGONISTS

CROSS-REFERENCE TO RELATED APPLICATIONS

This Application claims priority to U.S. Provisional Patent Application No. 60/623,053, filed Oct. 28, 2004, which is hereby incorporated by reference in its entirety.

FIELD OF THE INVENTION

This invention is directed to certain novel [1,4]benzodiazepine compounds, their synthesis, and their use as vasopressin V2 receptor antagonists. More particularly, the compounds of the present invention interfere with the binding of the peptide hormone, vasopressin, to its receptors and are therefore useful for treating conditions involving increased vascular resistance, cardiac insufficiency, and water retention.

BACKGROUND OF THE INVENTION

Vasopressin is a nonapeptide hormone that is secreted primarily from the posterior pituitary gland. The hormone effects its actions through membrane-bound V-1 and V-2 receptor subtypes. The functions of vasopressin include contraction of uterine, bladder, and smooth muscle; stimulation of glycogen breakdown in the liver; release of corticotropin from the anterior pituitary; induction of platelet aggregation; and central nervous system modulation of behaviors and stress responses. The V-1 receptor mediates the contraction of smooth muscle, and hepatic glycogenolytic and central nervous system effects of vasopressin. The V-2 receptor, presumably found only in the kidney, effects the antidiuretic actions of vasopressin via stimulation of adenylate cyclase.

Elevated plasma vasopressin levels appear to play a role in the pathogenesis of congestive heart failure (P. A. Van Zwieten, *Progr. Pharmacol. Clin. Pharmacol.* 1990, 7, 49). As progress toward the treatment of congestive heart failure, nonapeptide vasopressin V-2 receptor antagonists have induced low osmolality aquaresis and decreased peripheral resistance in conscious dogs with congestive heart failure (H. Ogawa, *J. Med. Chem.* 1996, 39, 3547). In certain pathological states, plasma vasopressin levels may be inappropriately elevated for a given osmolality, thereby resulting in renal water retention and hyponatremia. Hyponatremia, associated with edematous conditions (cirrhosis, congestive heart failure, renal failure), can be accompanied by the syndrome of inappropriate secretion of antidiuretic hormone (SIADH). Treatment of SIADH-compromised rats with a vasopressin V-2 antagonist has corrected their existing hyponatremia (G. Fujisawa, *Kidney Int.* 1993, 44(1), 19). Due in part to the contractile actions of vasopressin at the V-1 receptor in the vasculature, vasopressin V-1 receptor antagonists have reduced blood pressure as a potential treatment for hypertension. Thus, vasopressin receptor antagonists may be useful as therapeutics in the conditions of hypertension, congestive heart failure/cardiac insufficiency, coronary vasospasm, cardiac ischemia, liver cirrhosis, renal vasospasm, renal failure, cerebral edema and ischemia, stroke, thrombosis, and water retention.

It is an object of the present invention to provide vasopressin V2 receptor modulators. It is a further object of the invention to provide vasopressin V2 receptor antagonists. It is also an object of the invention to provide a method of treating or ameliorating a condition mediated by a vasopressin V2 receptor. And, it is an object of the invention to provide a useful pharmaceutical composition comprising a compound of the present invention useful as a vasopressin V2 receptor modulator.

SUMMARY OF THE INVENTION

The present invention is directed to bicyclic [1,4]benzodiazepine compounds of Formula (I):

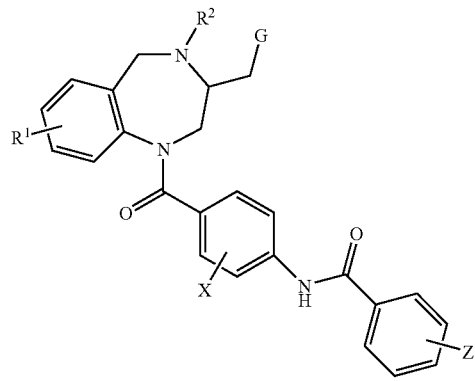

Formula (I)

wherein:

$R^1$ is independently selected from the group consisting of hydrogen, $C_{1-6}$alkyl, $C_{1-6}$alkoxy, and one to three halogen atoms;

$R^2$ is independently selected from the group consisting of hydrogen, $C_{1-6}$alkyl, aryl($C_{1-6}$)alkyl, cycloalkyl($C_{1-6}$)alkyl, ($C_{1-6}$)alkylsulfonyl, arylsulfonyl, and $C_{1-6}$alkylcarbonyl;

G is independently selected from the group consisting of $C_{1-8}$alkyl, $C_{1-8}$alkoxy, $C_{3-10}$cycloalkoxy, $C_{1-8}$alkylcarbonyloxy, hydroxy, heterocyclyl, $C_{1-6}$alkylthio, $C_{1-6}$alkylsulfonyloxy, arylsulfonyloxy, and $NR^aR^b$;

$R^a$ and $R^b$ are independently selected from the group consisting of hydrogen and $C_{1-6}$alkyl, or, $R^a$ and $R^b$ are taken with the nitrogen atom to which they are both attached to form a 3 to 7 membered monocyclic heterocycle;

provided that when $R^2$ is hydrogen or $C_{1-6}$alkyl, G is other than $C_{1-8}$alkyl, $C_{1-8}$alkoxy, hydroxy, $C_{1-6}$alkylsulfonyloxy, $C_{1-8}$alkylcarbonyloxy, or $NR^aR^b$; such that $R^a$ and $R^b$ are not taken together to form a 3 to 7 membered monocyclic heterocycle;

X is independently selected from the group consisting of hydrogen, $C_{1-6}$alkyl, $C_{1-6}$alkoxy, and halogen;

Z is one to three substituents independently selected from the group consisting of $C_{1-6}$alkyl, $C_{1-6}$alkoxy, $C_{1-6}$alkylthio, halogen, hydroxy, nitro, and aryl, wherein said aryl is optionally substituted with one to five substituents independently selected from the group consisting of $C_{1-6}$alkyl, $C_{1-6}$alkoxy, hydroxy, $C_{1-6}$alkylthio, and halogen; and wherein the $C_{1-6}$alkyl and $C_{1-6}$alkoxy substituents of Z are optionally fluorinated, preferably with one to thirteen fluorine atoms;

and pharmaceutically acceptable enantiomers, diastereomers, racemates, solvates, hydrates, polymorphs, and salts thereof.

Illustrative of the invention is a pharmaceutical composition comprising a pharmaceutically acceptable carrier and any of the compounds described above.

The present invention is also directed to methods for producing the instant compounds of Formula (I) and pharmaceutical compositions and medicaments thereof.

The present invention is further directed to methods for treating vasopressin V2 modulated disorders such as conditions involving increased vascular resistance and cardiac insufficiency. Compounds of the present invention are believed to provide advantages over other compounds by providing improved pharmacological profiles. Further specific embodiments of preferred compounds are provided hereinafter.

DETAILED DESCRIPTION OF THE INVENTION

Embodiments of the present invention include a method for treating vasopressin V2 mediated disorders such as cardiovascular disease, and for treating conditions associated with such disorders, such as aquaretics (known to those skilled in the art as an increase in urine volume and a decrease in urine osmolality). Treatment comprises administering to a subject in need thereof a therapeutically effective amount of a compound of Formula (I) or a pharmaceutical composition comprising a mixture of a compound of Formula (I) and a pharmaceutically acceptable carrier.

Embodiments of the present invention include the use of a compound of Formula (I) for the preparation of a medicament for treating vasopressin V2 mediated disorders in a subject in need thereof.

Embodiments of the present invention include those compounds wherein $R^1$ is independently selected from the group consisting of hydrogen, $C_{1-6}$alkyl, and one to two halogen atoms.

Embodiments of the present invention include those compounds wherein $R^1$ is independently selected from the group consisting of hydrogen, $C_{1-3}$alkyl, and one to two halogen atoms selected from the group consisting of chlorine and fluorine.

Embodiments of the present invention include those compounds wherein $R^1$ is independently selected from the group consisting of hydrogen, methyl, chlorine, and fluorine.

Embodiments of the present invention include those compounds wherein $R^2$ is independently selected from the group consisting of hydrogen, $C_{1-3}$alkyl, aryl($C_{1-3}$)alkyl, ($C_{1-3}$)alkylsulfonyl, arylsulfonyl, and $C_{1-3}$alkylcarbonyl; provided that when $R^2$ is hydrogen or $C_{1-3}$alkyl, G is a substituent other than $C_{1-8}$alkyl, $C_{1-8}$alkoxy, hydroxy, $C_{1-6}$alkylsulfonyloxy, $C_{1-8}$alkylcarbonyloxy, or $NR^aR^b$; such that $R^a$ and $R^b$ are not taken together to form a heterocycle.

Embodiments of the present invention include those compounds wherein $R^2$ is independently selected from the group consisting of hydrogen, methyl, propyl, methanesulfonyl, propanesulfonyl, benzenesulfonyl, and $C_{1-3}$alkylcarbonyl; provided that when $R^2$ is selected from hydrogen, methyl, or propyl, G is a substituent other than $C_{1-8}$alkyl, $C_{1-8}$alkoxy, hydroxy, $C_{1-6}$alkylsulfonyloxy, $C_{1-8}$alkylcarbonyloxy, or $NR^aR^b$; such that $R^a$ and $R^b$ are not taken together to form a heterocycle.

Embodiments of the present invention include those compounds wherein $R^2$ is independently selected from the group consisting of hydrogen, methyl, methanesulfonyl, and methylcarbonyl, provided that when $R^2$ is selected from hydrogen or methyl, G is a substituent other than $C_{1-8}$alkyl, $C_{1-8}$alkoxy, hydroxy, $C_{1-6}$alkylsulfonyloxy, $C_{1-8}$alkylcarbonyloxy, or $NR^aR^b$; such that $R^a$ and $R^b$ are not taken together to form a heterocycle.

Embodiments of the present invention include those compounds wherein G is independently selected from the group consisting of $C_{1-3}$alkyl, $C_{1-3}$alkoxy, $C_{3-8}$cycloalkoxy, $C_{1-3}$alkylcarbonyloxy, hydroxy, heterocyclyl, $C_{1-3}$alkylthio, $C_{1-3}$alkylsulfonyloxy, arylsulfonyloxy, and $NR^aR^b$; provided that when $R^2$ is hydrogen or $C_{1-6}$alkyl, G is other than $C_{1-3}$alkyl, $C_{1-3}$alkoxy, hydroxy, $C_{1-3}$alkylsulfonyloxy, $C_{1-3}$alkylcarbonyloxy, or $NR^aR^b$; such that $R^a$ and $R^b$ are not taken together to form a heterocycle.

Embodiments of the present invention include those compounds wherein G is independently selected from the group consisting of $C_{1-3}$alkyl, $C_{1-3}$alkoxy, $C_{1-3}$alkylcarbonyloxy, hydroxy, heterocyclyl, $C_{1-3}$alkylthio, $C_{1-3}$alkylsulfonyloxy, arylsulfonyloxy, and $NR^aR^b$; provided that when $R^2$ is hydrogen or $C_{1-6}$alkyl, G is other than $C_{1-3}$alkyl, $C_{1-3}$alkoxy, hydroxy, $C_{1-3}$alkylcarbonyloxy, $C_{1-3}$alkylsulfonyloxy, or $NR^aR^b$; such that $R^a$ and $R^b$ are not taken together to form a heterocycle.

Embodiments of the present invention include those compounds wherein G is independently selected from the group consisting of methoxy, methylcarbonyloxy, hydroxy, morpholino, methylthio, methanesulfonyloxy, benzenesulfonyloxy, and $NR^aR^b$; provided that when $R^2$ is hydrogen or $C_{1-6}$alkyl, G is other than methoxy, hydroxy, methylcarbonyloxy, methanesulfonyloxy, or $NR^aR^b$; such that $R^a$ and $R^b$ are not taken together to form a heterocycle.

Embodiments of the present invention include those compounds wherein G is independently selected from the group consisting of methoxy, methylcarbonyloxy, hydroxy, morpholino, methylthio, benzenesulfonyloxy, dimethylamino, and pyrrolidin-1-yl; provided that when $R^2$ is hydrogen or $C_{1-6}$alkyl, G is other than methoxy, hydroxy, methylcarbonyloxy, or dimethylamino.

Embodiments of the present invention include those compounds wherein when $R^2$ is as previously defined in one or more embodiments above and is other than hydrogen or $C_{1-6}$alkyl, G is independently selected from the group consisting of methoxy and hydroxy.

Embodiments of the present invention include those compounds wherein $R^a$ and $R^b$ are independently selected from the group consisting of hydrogen and $C_{1-3}$alkyl; or $R^a$ and $R^b$ are taken together with the nitrogen atom to which they are both attached to form a 3 to 7 membered monocyclic heterocycle.

Embodiments of the present invention include those compounds wherein X is independently selected from the group consisting of hydrogen, $C_{1-3}$alkyl, $C_{1-3}$alkoxy, and halogen.

Embodiments of the present invention include those compounds wherein X is independently selected from the group consisting of hydrogen, methyl, methoxy, chlorine, and fluorine.

Embodiments of the present invention include those compounds wherein X is independently selected from the group consisting of hydrogen, methoxy, and chlorine.

Embodiments of the present invention include those compounds wherein Z is one to three substituents independently selected from the group consisting of $C_{1-3}$alkyl, $C_{1-3}$alkoxy, $C_{1-3}$alkylthio, halogen, hydroxy, nitro, and aryl, wherein said aryl is optionally substituted with one to five substituents independently selected from the group consisting of $C_{1-3}$alkyl, $C_{1-3}$alkoxy, hydroxy, $C_{1-3}$alkylthio, and halogen; and wherein the $C_{1-3}$alkyl and $C_{1-3}$alkoxy substituents of Z are optionally fluorinated with one to seven fluorine atoms.

Embodiments of the present invention include those compounds wherein Z is one to two substituents independently selected from the group consisting of methyl, methoxy, methylthio, fluorine, chlorine, hydroxy, nitro, and phenyl, wherein said phenyl is optionally substituted with one to five substituents independently selected from the group consisting of methyl, methoxy, hydroxy, methylthio, fluorine, and chlorine; and wherein the methyl and methoxy substituents of Z are optionally fluorinated with one to three fluorine atoms. Preferably, at least one Z is phenyl or methyl and positioned ortho to the aminocarbonyl of Formula (I).

Embodiments of the present invention include those compounds wherein Z is one to two substituents independently selected from the group consisting of methyl, fluorine, chlorine, and phenyl, wherein said phenyl is optionally substituted with one to three substituents independently selected from the group consisting of methyl, methoxy, hydroxy, fluorine, and chlorine; and wherein the methyl and methoxy substituents of Z are optionally fluorinated with one to three fluorine atoms. Preferably, at least one Z is phenyl or methyl and positioned ortho to the aminocarbonyl of Formula (I).

Embodiments of the present invention include those compounds wherein Z is one to two substituents independently selected from the group consisting of methyl, fluorine, chlorine, and phenyl. Preferably, at least one Z is phenyl or methyl and positioned ortho to the aminocarbonyl of Formula (I). Most preferably, Z is phenyl positioned ortho to the aminocarbonyl of Formula (I).

An aspect of the present invention includes compounds of Formula (Ia)

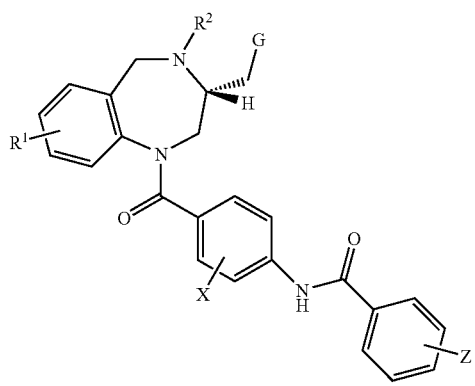

Formula (Ia)

wherein:
$R^1$ is independently selected from the group consisting of hydrogen, $C_{1-6}$alkyl, and one to two halogen atoms;
$R^2$ is independently selected from the group consisting of hydrogen, $C_{1-3}$alkyl, aryl($C_{1-3}$)alkyl, ($C_{1-3}$)alkylsulfonyl, arylsulfonyl, and $C_{1-6}$alkylcarbonyl;
G is independently selected from the group consisting of methoxy, methylcarbonyloxy, hydroxy, morpholino, methylthio, methanesulfonyloxy, benzenesulfonyloxy, and $NR^aR^b$;
  wherein $R^a$ and $R^b$ are independently selected from the group consisting of hydrogen and $C_{1-3}$alkyl; or, $R^a$ and $R^b$ are taken with the nitrogen atom to which they are both attached to form a 3 to 7 membered monocyclic heterocycle;
  provided that when $R^2$ is hydrogen or $C_{1-3}$alkyl, G is other than methoxy, hydroxy, methylcarbonyloxy, methanesulfonyloxy, or $NR^aR^b$; such that $R^a$ and $R^b$ are not taken together to form a heterocycle;
X is independently selected from the group consisting of hydrogen, $C_{1-3}$alkyl, $C_{1-3}$alkoxy, and halogen;
Z is one to two substituents independently selected from the group consisting of methyl, methoxy, methylthio, fluorine, chlorine, hydroxy, nitro, and phenyl, wherein said phenyl is optionally substituted with one to five substituents independently selected from the group consisting of methyl, methoxy, hydroxy, methylthio, fluorine, and chlorine; and wherein the methyl and methoxy substituents of Z are optionally fluorinated with one to three fluorine atoms; and at least one Z is phenyl or methyl and positioned ortho to the aminocarbonyl of Formula (Ia);

and pharmaceutically acceptable enantiomers, diastereomers, racemates, solvates, hydrates, polymorphs, and salts thereof.

Another aspect of the present invention includes compounds of Formula (Ia) wherein:
$R^1$ is independently selected from the group consisting of hydrogen, $C_{1-3}$alkyl, and one to two chlorine or fluorine atoms;
$R^2$ is independently selected from the group consisting of hydrogen, methyl, propyl, methanesulfonyl, propanesulfonyl, benzenesulfonyl, and $C_{1-3}$alkylcarbonyl;
G is independently selected from the group consisting of methoxy, methylcarbonyloxy, hydroxy, morpholino, methylthio, benzenesulfonyloxy, dimethylamino, and pyrrolidin-1-yl;
  provided that when $R^2$ is hydrogen, methyl or propyl, G is other than methoxy, hydroxy, methylcarbonyloxy, or dimethylamino;
X is independently selected from the group consisting of hydrogen, methyl, methoxy, chlorine, and fluorine;
Z is one to two substituents independently selected from the group consisting of methyl, fluorine, chlorine, and phenyl, wherein said phenyl is optionally substituted with one to three substituents independently selected from the group consisting of methyl, methoxy, hydroxy, fluorine, and chlorine; and wherein the methyl and methoxy substituents of Z are optionally fluorinated with one to three fluorine atoms; and preferably, at least one Z is phenyl or methyl and positioned ortho to the aminocarbonyl of Formula (Ia);

and pharmaceutically acceptable enantiomers, diastereomers, racemates, solvates, hydrates, polymorphs, and salts thereof.

A further aspect of the present invention includes compounds of Formula (Ia) wherein:
$R^1$ is independently selected from the group consisting of hydrogen, methyl, chlorine, and fluorine;
$R^2$ is independently selected from the group consisting of methanesulfonyl and methylcarbonyl;
G is independently selected from the group consisting of methoxy and hydroxy;
X is independently selected from the group consisting of hydrogen, methoxy, and chlorine;
Z is one to two substituents independently selected from the group consisting of methyl, fluorine, chlorine, and phenyl; preferably at least one Z is phenyl or methyl and positioned ortho to the aminocarbonyl of Formula (Ia);

and pharmaceutically acceptable enantiomers, diastereomers, racemates, solvates, hydrates, polymorphs, and salts thereof.

Exemplified compounds of the present invention include compounds of Formula (Ib):

Formula (Ib)

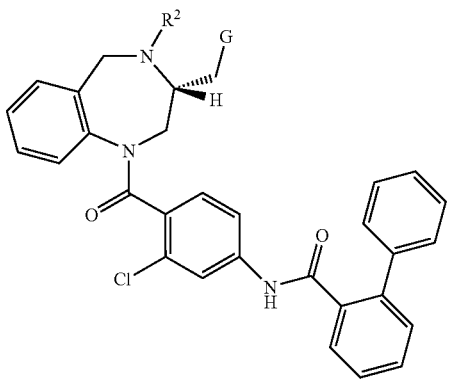

selected from the group consisting of:
a compound of Formula (Ib) wherein $R^2$ is $CH_2Ph$ and G is OH;
a compound of Formula (Ib) wherein $R^2$ is $CH_3$ and G is $SCH_3$;
a compound of Formula (Ib) wherein $R^2$ is $CH_3$ and G is

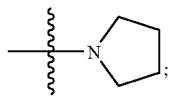

a compound of Formula (Ib) wherein $R^2$ is $CH_3$ and G is

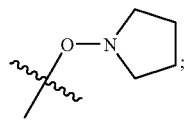

a compound of Formula (Ib) wherein $R^2$ is $CH_3$ and G is

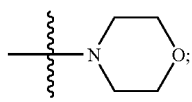

a compound of Formula (Ib) wherein $R^2$ is $CH_3$ and G is $OCH_3$;
a compound of Formula (Ib) wherein $R^2$ is $SO_2CH_3$ and G is OH;
a compound of Formula (Ib) wherein $R^2$ is $SO_2CH_3$ and G is $OSO_2CH_3$;
a compound of Formula (Ib) wherein $R^2$ is $C(=O)CH_3$ and G is $OC(=O)CH_3$;
a compound of Formula (Ib) wherein $R^2$ is $SO_2(CH_2)_2CH_3$ and G is OH;
a compound of Formula (Ib) wherein $R^2$ is $SO_2Ph$ and G is OH; and
a compound of Formula (Ib) wherein $R^2$ is $C(=O)CH_3$ and G is OH.

The compounds of the present invention may also be present in the form of pharmaceutically acceptable salts. For use in medicine, the salts of the compounds of this invention refer to non-toxic "pharmaceutically acceptable salts." Other salts may, however, be useful in the preparation of compounds according to this invention or of their pharmaceutically acceptable salts. Representative organic or inorganic acids include, but are not limited to, hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benezenesulfonic, oxalic, pamoic, 2-naphthalenesulfonic, p-toluenesulfonic, cyclohexanesulfamic, salicylic, saccharinic or trifluoroacetic acid.

Where the compounds according to this invention have at least one stereogenic center, they may accordingly exist as enantiomers. As indicated in Formulae Ia and Ib, the compounds of interest to this invention have a specific absolute configuration at the stereocenter on the benzodiazepine ring, in the manner shown. Where the compounds possess stereogenic centers in addition to this one, they may exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the subject. Conventional procedures for the selection and preparation of suitable prodrug derivatives are described, for example, in "*Design of Prodrugs*", ed. H. Bundgaard, Elsevier, 1985.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known in the art.

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. In general, under standard nomenclature rules used throughout this disclosure, the terminal portion of the designated side chain is described first followed by the adjacent functionality toward the point of attachment. Thus, for example, a "phenyl$C_1$-$C_6$ alkylamido$C_1$-$C_6$alkyl" substituent refers to a group of the formula:

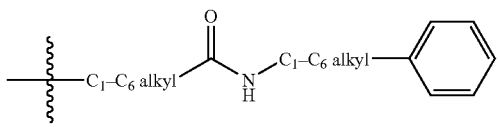

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

An "independently" selected substituent refers to a group of substituents, wherein the substituents may be different. Therefore, designated numbers of carbon atoms (e.g. $C_{1-8}$) shall refer independently to the number of carbon atoms in an alkyl or cycloalkyl moiety or to the alkyl portion of a larger substituent in which alkyl appears as its prefix root.

As used herein, unless otherwise noted, "alkyl" whether used alone or as part of a substituent group refers to straight and branched carbon chains having 1 to 8 carbon atoms or any number within this range. The term "alkoxy" refers to an —Oalkyl substituent group, wherein alkyl is as defined supra. Similarly, the terms "alkenyl" and "alkynyl" refer to straight and branched carbon chains having 2 to 8 carbon atoms or any number within this range, wherein an alkenyl chain has at least one double bond in the chain and an alkynyl chain has at least one triple bond in the chain. An alkyl and alkoxy chain may be substituted on a carbon atom. In substituent groups with multiple alkyl groups such as $(C_{1-6}alkyl)_2$amino—the $C_{1-6}$alkyl groups of the dialkylamino may be the same or different.

The term "cycloalkyl" refers to saturated or partially unsaturated, monocyclic or polycyclic hydrocarbon rings of from 3 to 20 carbon atom members (preferably from 3 to 14 carbon atom members). Further, a cycloalkyl ring may optionally be fused to one or more cycloalkyl rings. Examples of such rings include, and are not limited to, cyclopropyl, cyclobutyl, cyclopentyl, cyclohexyl, cycloheptyl or adamantyl. Alternatively, the cycloalkyl ring may be fused to a benzene ring (benzo fused cycloalkyl), a 5 or 6 membered heteroaryl ring (containing one of O, S or N and, optionally, one additional nitrogen) to form a heteroaryl fused cycloalkyl. The term "cycloalkoxy" refers to an —Ocycloalkyl substituent group, wherein cycloalkyl is as defined supra.

The term "heterocyclyl" refers to a nonaromatic cyclic ring of 5 to 10 members in which 1 to 4 members are nitrogen or a nonaromatic cyclic ring of 5 to 10 members in which zero, one or two members are nitrogen and up to two members is oxygen or sulfur; wherein, optionally, the ring contains zero, one or two unsaturated bonds. Alternatively, the heterocyclyl ring may be fused to a benzene ring (benzo fused heterocyclyl), a 5 or 6 membered heteroaryl ring (containing one of O, S or N and, optionally, one additional nitrogen), a 5 to 7 membered cycloalkyl or cycloalkenyl ring, a 5 to 7 membered heterocyclyl ring (of the same definition as above but absent the option of a further fused ring) or fused with the carbon of attachment of a cycloalkyl, cycloalkenyl or heterocyclyl ring to form a spiro moiety. For instant compounds of the invention, the carbon atom ring members that form the heterocyclyl ring are fully saturated. Other compounds of the invention may have a partially saturated heterocyclyl ring. Additionally, the heterocyclyl can be bridged to form bicyclic rings. Preferred partially saturated heterocyclyl rings may have from one to two double bonds. Such compounds are not considered to be fully aromatic and are not referred to as heteroaryl compounds. Examples of heterocyclyl groups include, and are not limited to, pyrrolinyl (including 2H-pyrrole, 2-pyrrolinyl or 3-pyrrolinyl), pyrrolidinyl, 2-imidazolinyl, imidazolidinyl, 2-pyrazolinyl, pyrazolidinyl, piperidinyl, morpholinyl, thiomorpholinyl and piperazinyl.

The term "aryl" refers to an unsaturated, aromatic monocyclic ring of 6 carbon members or to an unsaturated, aromatic polycyclic ring of from 10 to 20 carbon members. Examples of such aryl rings include, and are not limited to, phenyl, naphthalenyl or anthracenyl. Preferred aryl groups for the practice of this invention are phenyl and naphthalenyl.

The term "heteroaryl" refers to an aromatic ring of 5 or 6 members wherein the ring consists of carbon atoms and has at least one heteroatom member. Suitable heteroatoms include nitrogen, oxygen or sulfur. In the case of 5 membered rings, the heteroaryl ring contains one member of nitrogen, oxygen or sulfur and, in addition, may contain up to three additional nitrogens. In the case of 6 membered rings, the heteroaryl ring may contain from one to three nitrogen atoms. For the case wherein the 6 membered ring has three nitrogens, at most two nitrogen atoms are adjacent. Optionally, the heteroaryl ring is fused to a benzene ring (benzo fused heteroaryl), a 5 or 6 membered heteroaryl ring (containing one of O, S or N and, optionally, one additional nitrogen), a 5 to 7 membered cycloalkyl ring or a 5 to 7 membered heterocyclo ring (as defined supra but absent the option of a further fused ring). Examples of heteroaryl groups include, and are not limited to, furyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl or pyrazinyl; fused heteroaryl groups include indolyl, isoindolyl, indolinyl, benzofuryl, benzothienyl, indazolyl, benzimidazolyl, benzthiazolyl, benzoxazolyl, benzisoxazolyl, benzothiadiazolyl, benzotriazolyl, quinolizinyl, quinolinyl, isoquinolinyl or quinazolinyl.

The term "arylalkyl" means an alkyl group substituted with an aryl group (e.g., benzyl, phenethyl). Similarly, the term "arylalkoxy" indicates an alkoxy group substituted with an aryl group (e.g., benzyloxy).

The term "halogen" refers to fluorine, chlorine, bromine and iodine. Substituents that are substituted with multiple halogens are substituted in a manner that provides compounds, which are stable.

Whenever the term "alkyl" or "aryl" or either of their prefix roots appear in a name of a substituent (e.g., arylalkyl, alkylamino) it shall be interpreted as including those limitations given above for "alkyl" and "aryl." Designated numbers of carbon atoms (e.g., $C_1$-$C_6$) shall refer independently to the number of carbon atoms in an alkyl moiety or to the alkyl portion of a larger substituent in which alkyl appears as its prefix root. For alkyl and alkoxy substituents, the designated number of carbon atoms includes all of the independent members included in the range specified individually and all the combination of ranges within in the range specified. For example $C_{1-6}$ alkyl would include methyl, ethyl, propyl, butyl, pentyl and hexyl individually as well as sub-combinations thereof (e.g. $C_{1-2}$, $C_{1-3}$, $C_{1-4}$, $C_{1-5}$, $C_{2-6}$, $C_{3-6}$, $C_{4-6}$, $C_{5-6}$, $C_{2-5}$, etc.).

The compounds of the present invention are useful vasopressin V2 receptor modulators. In particular, certain compounds are vasopressin V2 receptor antagonists useful in the treatment or amelioration of conditions such as hypertension, congestive heart failure, cardiac insufficiency, coronary vasospasm, cardiac ischemia, liver cirrhosis, renal vasospasm, renal failure, cerebral edema and ischemia, stroke, thrombosis, or water retention.

The utility of the compounds to treat disorders of increased vascular resistance can be determined according to the procedures described herein. The present invention therefore provides a method of treating vascular resistance disorders in a subject in need thereof which comprises administering any of the compounds as defined herein in a quantity effective to treat vascular resistance disorders. A compound may be administered to a patient in need of treatment by any conventional route of administration including, but not limited to oral, nasal, sublingual, ocular, transdermal, rectal, vaginal and parenteral (i.e. subcutaneous, intramuscular, intradermal, intravenous etc.).

The present invention also provides pharmaceutical compositions comprising one or more compounds of this invention in association with a pharmaceutically acceptable carrier.

To prepare the pharmaceutical compositions of this invention, one or more compounds of formula (I) or salt thereof as the active ingredient, is intimately admixed with a pharmaceutical carrier according to conventional pharmaceutical compounding techniques, which carrier may take a wide variety of forms depending of the form of preparation desired for administration (e.g. oral or parenteral such as intramuscular). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

Methods of formulating pharmaceutical compositions have been described in numerous publications such as *Pharmaceutical Dosage Forms: Tablets, Second Edition, Revised and Expanded*, Volumes 1-3, edited by Lieberman et al; *Pharmaceutical Dosage Forms: Parenteral Medications*, Volumes 1-2, edited by Avis et al; and *Pharmaceutical Dosage Forms: Disperse Systems*, Volumes 1-2, edited by Lieberman et al; published by Marcel Dekker, Inc.

In preparing a pharmaceutical composition of the present invention in liquid dosage form for oral, topical and parenteral administration, any of the usual pharmaceutical media or excipients may be employed. Thus, for liquid dosage forms, such as suspensions (i.e. colloids, emulsions and dispersions) and solutions, suitable carriers and additives include but are not limited to pharmaceutically acceptable wetting agents, dispersants, flocculation agents, thickeners, pH control agents (i.e. buffers), osmotic agents, coloring agents, flavors, fragrances, preservatives (i.e. to control microbial growth, etc.) and a liquid vehicle may be employed. Not all of the components listed above will be required for each liquid dosage form.

In solid oral preparations such as, for example, powders, granules, capsules, caplets, gelcaps, pills and tablets (each including immediate release, timed release and sustained release formulations), suitable carriers and additives include but are not limited to diluents, granulating agents, lubricants, binders, glidants, disintegrating agents and the like. Because of their ease of administration, tablets and capsules represent the most advantageous oral dosage unit form, in which case solid pharmaceutical carriers are obviously employed. If desired, tablets may be sugar coated, gelatin coated, film coated or enteric coated by standard techniques.

The pharmaceutical compositions herein will contain, per dosage unit, e.g., tablet, capsule, powder, injection, teaspoonful and the like, an amount of the active ingredient necessary to deliver an effective dose as described above. The therapeutically effective amount of the compounds of Formula (I) exemplified in such a method is from about 0.01 mg/kg/day to about 300 mg/kg/day. Particularly, the range is from about 0.5 to about 5.0 mg/kg of body weight per day; and more particularly, from about 1.0 to about 3.0 mg/kg of body weight per day. The compounds may be administered on a regimen of 1 to 4 times per day.

Preferably, for the method of treating vascular resistance disorders described in the present invention using any of the compounds as defined herein, the dosage form will contain a pharmaceutically acceptable carrier containing between about 0.01 mg and 100 mg, more preferably about 5 to 50 mg, of the compound, and may be constituted into any form suitable for the mode of administration selected. The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, lozenges, sterile parenteral solutions or suspensions, metered aerosol or liquid sprays, drops, ampoules, autoinjector devices or suppositories; for administration by oral, intranasal, sublingual, intraocular, transdermal, parenteral, rectal, vaginal, inhalation or insufflation means. Alternatively, the composition may be presented in a form suitable for onceweekly or once-monthly administration; for example, an insoluble salt of the active compound, such as the decanoate salt, may be adapted to provide a depot preparation for intramuscular injection.

For preparing solid pharmaceutical compositions such as tablets, the principal active ingredient is mixed with a pharmaceutical carrier, e.g. conventional tableting ingredients such as diluents, binders, adhesives, disintegrants, lubricants, antiadherents and gildants. Suitable diluents include, but are not limited to, starch (i.e. corn, wheat, or potato starch, which may be hydrolized), lactose (granulated, spray dried or anhydrous), sucrose, sucrose-based diluents (confectioner's sugar; sucrose plus about 7 to 10 weight percent invert sugar; sucrose plus about 3 weight percent modified dextrins; sucrose plus invert sugar, about 4 weight percent invert sugar, about 0.1 to 0.2 weight percent cornstarch and magnesium stearate), dextrose, inositol, mannitol, sorbitol, microcrystalline cellulose (i.e. AVICEL™ microcrystalline cellulose available from FMC Corp.), dicalcium phosphate, calcium sulfate dihydrate, calcium lactate trihydrate and the like. Suitable binders and adhesives include, but are not limited to accacia gum, guar gum, tragacanth gum, sucrose, gelatin, glucose, starch, and cellulosics (i.e. methylcellulose, sodium carboxymethycellulose, ethylcellulose, hydroxypropylmethylcellulose, hydroxypropylcellulose, and the like), water soluble or dispersible binders (i.e. alginic acid and salts thereof, magnesium aluminum silicate, hydroxyethylcellulose [i.e. TYLOSE™ available from SE TYLOSE GmbH & Co. KG], polyethylene glycol, polysaccharide acids, bentonites, polyvinylpyrrolidone, polymethacrylates and pregelatinized starch) and the like. Suitable disintegrants include, but are not limited to, starches (corn, potato, etc.), sodium starch glycolates, pregelatinized starches, clays (magnesium aluminum silicate), celluloses (such as crosslinked sodium carboxymethylcellulose and microcrystalline cellulose), alginates, pregelatinized starches (i.e. corn starch, etc.), gums (i.e. agar, guar, locust bean, karaya, pectin, and tragacanth gum), cross-linked polyvinylpyrrolidone and the like. Suitable lubricants and antiadherents include, but are not limited to, stearates (magnesium, calcium and sodium), stearic acid, talc waxes, stearowet, boric acid, sodium chloride, DL-leucine, carbowax 4000, carbowax 6000, sodium oleate, sodium benzoate, sodium acetate, sodium lauryl sulfate, magnesium lauryl sulfate and the like. Suitable gildants include, but are not limited to, talc, cornstarch, silica (i.e. CAB-O-SIL™ silica available from Cabot, SYLOID™ silica available from W.R. Grace/Davison, and AEROSIL™ silica available from Degussa) and the like. Sweeteners and flavorants may be added to chewable solid dosage forms to improve the palatability of the oral dosage form. Additionally, colorants and coatings may be added or applied to the solid dosage form for ease of identification of the drug or for aesthetic purposes. These carriers are formulated with the pharmaceutical active to provide a accurate, appropriate dose of the pharmaceutical active with a therapeutic release profile.

Generally these carriers are mixed with the pharmaceutical active to form a solid preformulation composition containing a homogeneous mixture of the pharmaceutical active of the present invention, or a pharmaceutically acceptable salt thereof. Generally the preformulation will be formed by one of three common methods: (a) wet granulation, (b) dry granulation and (c) dry blending. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from about 0.1 mg to about 500 mg of the active ingredient of the present invention. The tablets or pills containing the novel compositions may also be formulated in multilayer tablets or pills to provide a sustained or provide dual-release products. For example, a dual release tablet or pill can comprise an inner dosage and an outer dosage component, the latter being in the form of an envelope over the former. The two components can be separated by an enteric layer, which serves to resist disintegration in the stomach and permits the inner component to pass intact into the duodenum or to be delayed in release. A variety of materials can be used for such enteric layers or coatings, such materials including a number of polymeric materials such as shellac, cellulose acetate (i.e. cellulose acetate phthalate, cellulose acetate trimetllitate), polyvinyl acetate phthalate, hydroxypropyl methylcellulose phthalate, hydroxypropyl methylcellulose acetate succinate, methacrylate and ethylacrylate copolymers, methacrylate and methyl methacrylate copolymers and the like. Sustained release tablets may also be made by film coating or wet granulation using slightly soluble or insoluble substances in solution (which for a wet granulation acts as the binding agents) or low melting solids a molten form (which in a wet granulation may incorporate the active ingredient). These materials include natural and synthetic polymers waxes, hydrogenated oils, fatty acids and alcohols (i.e. beeswax, carnauba wax, cetyl alcohol, cetylstearyl alcohol, and the like), esters of fatty acids metallic soaps, and other acceptable materials that can be used to granulate, coat, entrap or otherwise limit the solubility of an active ingredient to achieve a prolonged or sustained release product.

The liquid forms in which the novel compositions of the present invention may be incorporated for administration orally or by injection include, but are not limited to aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable suspending agents for aqueous suspensions, include synthetic and natural gums such as, acacia, agar, alginate (i.e. propylene alginate, sodium alginate and the like), guar, karaya, locust bean, pectin, tragacanth, and xanthan gum, cellulosics such as sodium carboxymethylcellulose, methylcellulose, hydroxymethylcellulose, hydroxyethylcellulose, hydroxypropyl cellulose and hydroxypropyl methylcellulose, and combinations thereof, synthetic polymers such as polyvinyl pyrrolidone, carbomer (i.e. carboxypolymethylene), and polyethylene glycol; clays such as bentonite, hectorite, aftapulgite or sepiolite; and other pharmaceutically acceptable suspending agents such as lecithin, gelatin or the like. Suitable surfactants include but are not limited to sodium docusate, sodium lauryl sulfate, polysorbate, octoxynol-9, nonoxynol-10, polysorbate 20, polysorbate 40, polysorbate 60, polysorbate 80, polyoxamer 188, polyoxamer 235 and combinations thereof. Suitable deflocculating or dispersing agent include pharmaceutical grade lecithins. Suitable flocculating agent include but are not limited to simple neutral electrolytes (i.e. sodium chloride, potassium, chloride, and the like), highly charged insoluble polymers and polyelectrolyte species, water soluble divalent or trivalent ions (i.e. calcium salts, alums or sulfates, citrates and phosphates (which can be used jointly in formulations as pH buffers and flocculating agents). Suitable preservatives include but are not limited to parabens (i.e. methyl, ethyl, propyl and butyl), sorbic acid, thimerosal, quaternary ammonium salts, benzyl alcohol, benzoic acid, chlorhexidine gluconate, phenylethanol and the like. There are many liquid vehicles that may be used in liquid pharmaceutical dosage forms, however, the liquid vehicle that is used in a particular dosage form must be compatible with the suspending agent(s). For example, nonpolar liquid vehicles such as fatty esters and oils liquid vehicles are best used with suspending agents such as low HLB (Hydrophile-Lipophile Balance) surfactants, stearalkonium hectorite, water insoluble resins, water insoluble film forming polymers and the like. Conversely, polar liquids such as water, alcohols, polyols and glycols are best used with suspending agents such as higher HLB surfactants, clays silicates, gums, water soluble cellulosics, water soluble polymers and the like. For parenteral administration, sterile suspensions and solutions are desired. Liquid forms useful for parenteral administration include sterile solutions, emulsions and suspensions. Isotonic preparations that generally contain suitable preservatives are employed when intravenous administration is desired.

Furthermore, compounds of the present invention can be administered in intranasal form via topical use of suitable intranasal vehicles, or via transdermal skin patches the composition of which are well known to those of ordinary skill in that art. To be administered in the form of a transdermal delivery system, the administration of a therapeutic dose will, of course, be continuous rather than intermittent throughout the dosage regimen.

Compounds of the present invention can also be administered in the form of liposome delivery systems, such as small unilamellar vesicles, large unilamellar vesicles, multilamellar vesicles and the like. Liposomes can be formed from a variety of phospholipids, such as cholesterol, stearylamine, phophatidylcholines and the like.

Compounds of the present invention may also be delivered by the use of monoclonal antibodies as individual carriers to which the compound molecules are coupled. The compounds of the present invention may also be coupled with soluble polymers as targetable drug carriers. Such polymers can include, but are not limited to polyvinylpyrrolidone, pyran copolymer, polyhydroxypropylmethacrylamidephenol, polyhydroxy-ethylaspartamidephenol, or polyethyl eneoxidepolylysine substituted with palmitoyl residue. Furthermore, the compounds of the present invention may be coupled to a class of biodegradable polymers useful in achieving controlled release of a drug, for example, to homopolymers and copolymers (which means polymers containing two or more chemically distinguishable repeating units) of lactide (which includes lactic acid d-, l- and meso lactide), glycolide (including glycolic acid), ε-caprolactone, p-dioxanone (1,4-dioxan-2-one), trimethylene carbonate (1,3-dioxan-2-one), alkyl derivatives of trimethylene carbonate, δ-valerolactone, β-butyrolactone, γ-butyrolactone, ε-decalactone, hydroxybutyrate, hydroxyvalerate, 1,4-dioxepan-2-one (including its dimer 1,5,8,12-tetraoxacyclotetradecane-7,14-dione), 1,5-dioxepan-2-one, 6,6-dimethyl-1,4-dioxan-2-one, polyorthoesters, polyacetals, polydihydropyrans, polycyanoacrylates and cross-linked or amphipathic block copolymers of hydrogels and blends thereof.

Where the processes for the preparation of the compounds according to the invention give rise to mixtures of stereoisomers, these isomers may be separated by conventional techniques such as preparative chromatography. The compounds may be prepared as single enantiomers either by enantiospecific synthesis or by classical resolution. The compounds may, for example, be resolved from racemates into component enantiomers by standard techniques, such as the formation of diastereomeric pairs by salt formation. The compounds may also be resolved by formation of diastereomeric esters or amides, followed by chromatographic separation and removal of the chiral auxiliary. Alternatively, the compounds may be resolved using a chiral HPLC column.

Compounds of this invention may be administered in any of the foregoing compositions and according to dosage regimens established in the art whenever treatment of disorders of vascular resistance is required for a subject.

The daily dose of a pharmaceutical composition of the present invention may be varied over a wide range from about 0.1 to 20,000 mg per adult human per day, however the dose will preferably be in the range of from about 1 to about 1,000 mg per adult human per day. For oral administration, the compositions are preferably provided in the form of tablets containing 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the subject to be treated. An effective amount of the drug is ordinarily supplied at a dosage level of from about 0.01 mg/kg/day to about 300 mg/kg/day. Particularly, the range is from about 0.5 to about 5.0 mg/kg of body weight per day; and more particularly, from about 1.0 to about 3.0 mg/kg of body weight per day. The compounds may be administered on a regimen of 1 to 4 times per day.

Optimal dosages to be administered may be readily determined by those skilled in the art, and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level.

Abbreviations used in the instant specification, particularly the Schemes and Examples, are as follows:

| | |
|---|---|
| Bn = | Benzyl |
| Boc = | t-Butoxycarbonyl |
| Cbz = | Benzyloxycarbonyl |
| Cpd = | Compound |
| DCM = | Dichloromethane |
| DIPEA = | Diisopropylethylamine |
| DMAP = | 4-Dimethylaminopyridine |
| DMF = | N,N-Dimethylformamide |
| DMSO = | Dimethylsulfoxide |

-continued

| | |
|---|---|
| Et$_2$O = | Diethyl ether |
| EtOAc = | Ethyl acetate |
| EtOH = | Ethanol |
| HPLC = | High Performance Liquid Chromatography |
| i-Pr = | Isopropyl |
| LAH = | Lithium aluminum hydride |
| Me = | Methyl |
| MeOH = | Methanol |
| MPK = | Milligrams per kilogram |
| NT = | Not tested |
| Ph = | Phenyl |
| Ppt = | Precipitate |
| RT or rt = | Room temperature |
| TEA = | Triethylamine |
| THF = | Tetrahydrofuran |
| TFA = | Trifluoroacetic acid |

General Synthetic Methods

Representative compounds of the present invention can be synthesized in accordance with the general synthetic methods described below and are illustrated more particularly in the schemes that follow. Since the schemes are illustrations whereby intermediate and target compounds of the present invention may be prepared, the invention should not be construed as being limited by the chemical reactions and conditions expressed. Additional representative compounds and stereoisomers, racemic mixtures, diastereomers and enantiomers thereof can be synthesized using the intermediates prepared in accordance with these schemes and other materials, compounds and reagents known to those skilled in the art. All such compounds, stereoisomers, racemic mixtures, diastereomers and enantiomers thereof are intended to be encompassed within the scope of the present invention. The preparation of the various starting materials used in the schemes is well within the skill of persons versed in the art.

Certain intermediates and compounds of the present invention may be prepared according to the processes outlined in Schemes A through C below.

In Scheme A, an R$^1$-substituted isatoic anhydride of formula A1 (available either commercially or prepared by protocols reported in the scientific literature) may be condensed with R-serine A2 under basic conditions with heat. Subsequent addition of L-tartaric acid with continued heating provides benzodiazepine-diones of formula A3 wherein R$^2$ is H. One versed in the art will recognize that the compounds of Scheme A and of the present invention can be synthesized with the opposite stereochemistry by condensing A1 with S-serine under similar reaction conditions and carrying out the synthetic sequence accordingly.

Scheme A

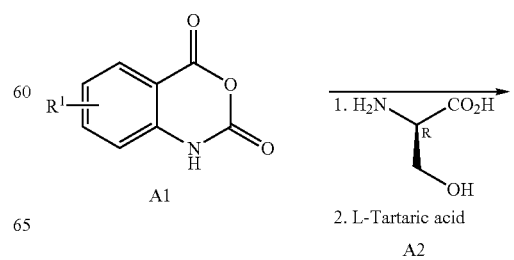

-continued

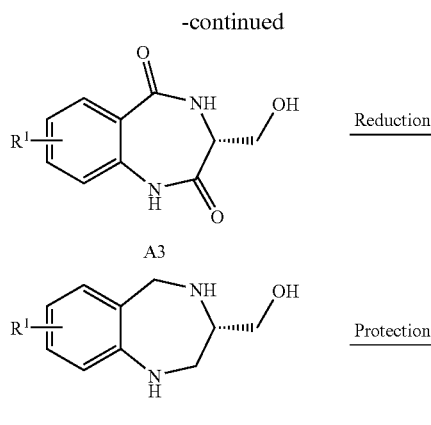

A3

Reduction →

A4

Protection →

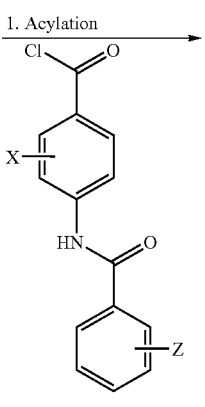

A5

1. Acylation

<chemical structure shown>

A6

2. Deprotection

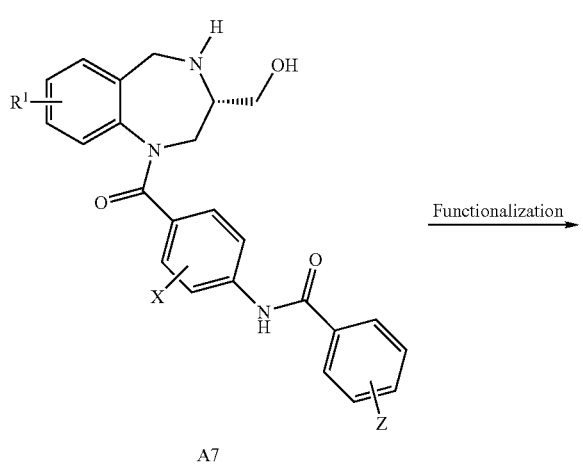

A7

Functionalization →

-continued

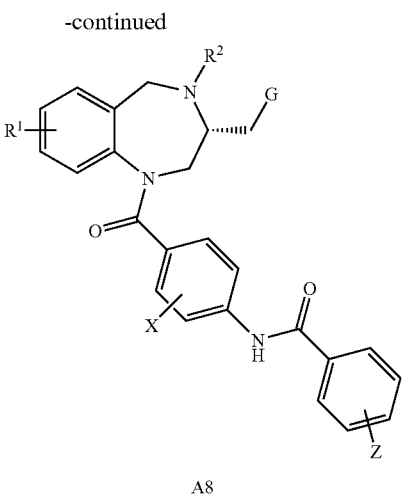

A8

Compounds of formula A3 may be reduced in the presence of a hydride source such as lithium aluminum hydride or the like in anhydrous ether solvent to give compounds of the formula A4. Compounds of formula A4 may be protected with an appropriate amino protecting group (PG) to give a compound of formula A5. At this stage, the available amino group may be acylated with a compound of Formula A6. Subsequent removal of the amino protecting group (PG) by conventional methods gives compounds of formula A7. The compounds of formula A7 may be derivatized to give compounds of Formula A8. For example, $R^2$ may be installed via sulfonylation, acylation, or reductive amination, while G may be installed via sulfonylation, acylation, or the nucleophilic displacement of a reactive precursor to G, such as a chloride, iodide, mesylate, or the like.

As shown in Scheme B, compounds of formula A6 may be prepared using standard acylation chemistry known to those skilled in the art. A Z-substituted benzoic acid of formula aa1 may be converted to its corresponding acid chloride using conventional reagents such as thionyl chloride or oxalyl chloride with trace catalytic DMF in a hydrocarbon solvent at temperatures below 10° C. An X-substituted amino benzoic acid of formula aa3 may be acylated with the acid chloride described herein in the presence of a base, such as pyridine, and trimethylchlorosilane at temperatures below 10° C. to afford compounds of formula aa4.

Scheme B

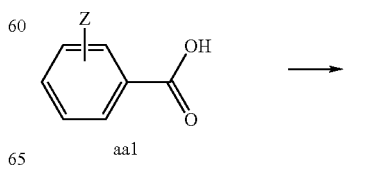

aa1

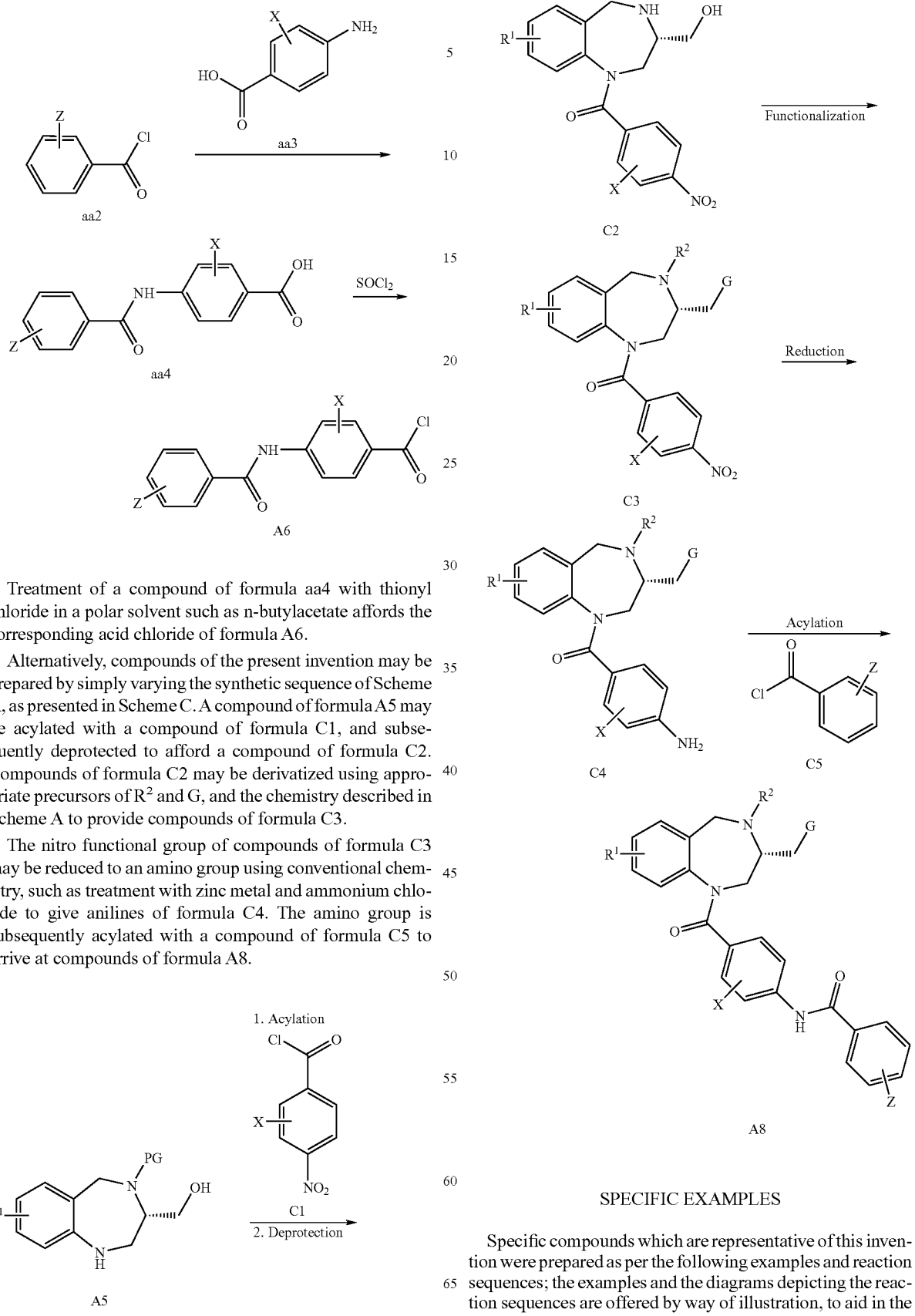

Treatment of a compound of formula aa4 with thionyl chloride in a polar solvent such as n-butylacetate affords the corresponding acid chloride of formula A6.

Alternatively, compounds of the present invention may be prepared by simply varying the synthetic sequence of Scheme A, as presented in Scheme C. A compound of formula A5 may be acylated with a compound of formula C1, and subsequently deprotected to afford a compound of formula C2. Compounds of formula C2 may be derivatized using appropriate precursors of $R^2$ and G, and the chemistry described in Scheme A to provide compounds of formula C3.

The nitro functional group of compounds of formula C3 may be reduced to an amino group using conventional chemistry, such as treatment with zinc metal and ammonium chloride to give anilines of formula C4. The amino group is subsequently acylated with a compound of formula C5 to arrive at compounds of formula A8.

SPECIFIC EXAMPLES

Specific compounds which are representative of this invention were prepared as per the following examples and reaction sequences; the examples and the diagrams depicting the reaction sequences are offered by way of illustration, to aid in the understanding of the invention and should not be construed to limit in any way the invention set forth in the claims which follow thereafter. The instant compounds may also be used as intermediates in subsequent examples to produce additional compounds of the present invention. No attempt has been made to optimize the yields obtained in any of the reactions. One skilled in the art would know how to increase such yields through routine variations in reaction times, temperatures, solvents and/or reagents.

Reagents were purchased from commercial sources. Microanalyses were performed at Robertson Microlit Laboratories, Inc., Madison, N.J. and are expressed in percentage by weight of each element per total molecular weight. Nuclear magnetic resonance (NMR) spectra for hydrogen atoms were measured in the indicated solvent with (TMS) as the internal standard on a Bruker Avance (500 MHz) spectrometer. The values are expressed in parts per million downfield from TMS. The mass spectra (MS) were determined on a Micromass Platform LC spectrometer as (ESI) m/z (M+H$^+$) using an electrospray technique. Optical rotations were obtained on a Perkin-Elmer polarimeter using the sodium D line as wavelength of light. Stereoisomeric compounds may be characterized as racemic mixtures or as separate diastereomers and enantiomers thereof using X-ray crystallography and other methods known to one skilled in the art. Unless otherwise noted, the materials used in the examples were obtained from readily available commercial suppliers or synthesized by standard methods known to one skilled in the art of chemical synthesis. The substituent groups, which vary between examples, are hydrogen unless otherwise noted.

Example AA

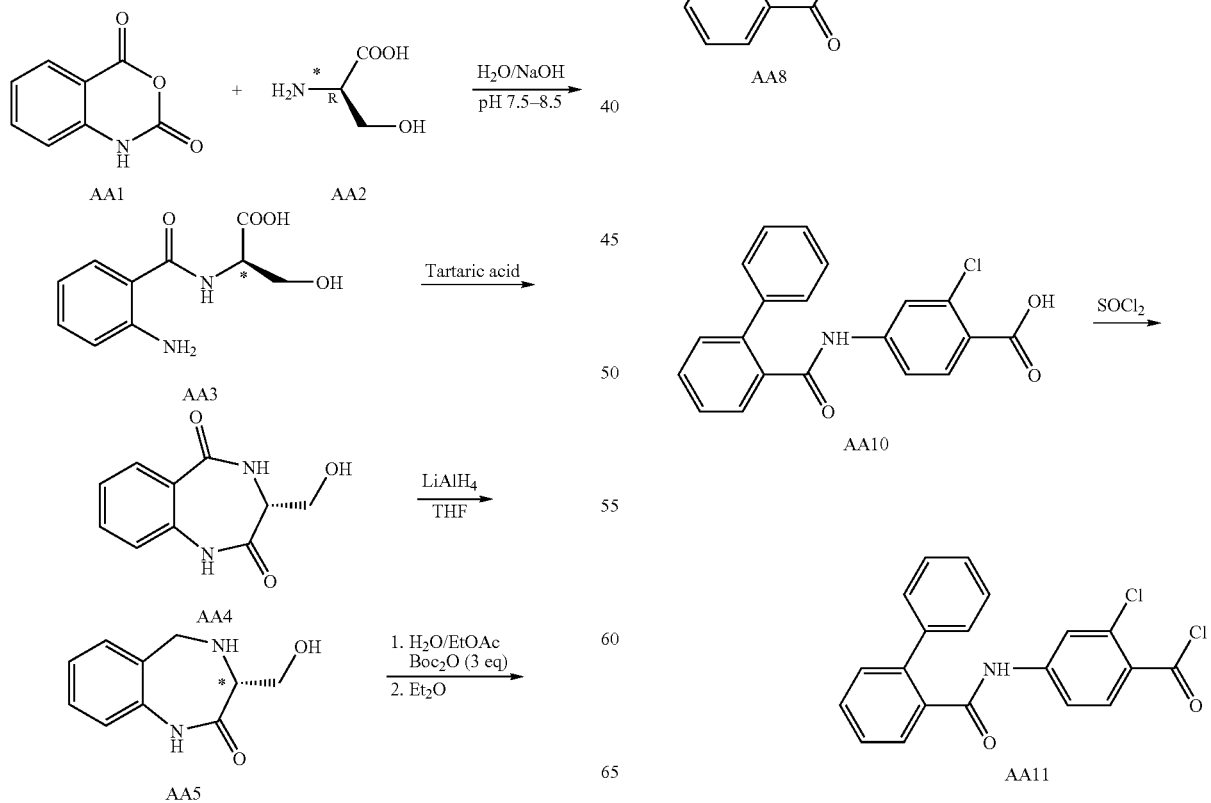

-continued

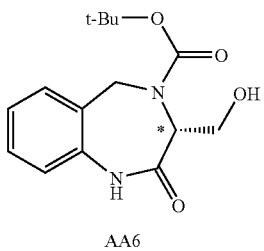

AA6

Cpd AA6 
1. DIPEA, Cpd AA11
2. HCl
3. NH₃
→

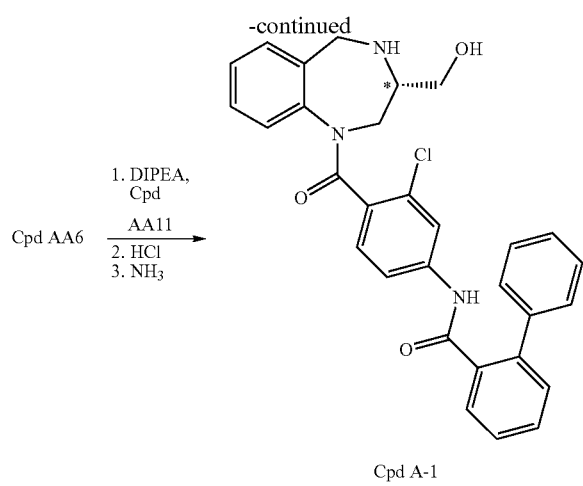

Cpd A-1

A. 3R-Hydroxymethyl-1,4-benzodiazepine-2,5-dione. To a colorless suspension of R-Serine (102.3 g, 0.974 mol, 100%) in water (335.0 g, 18.95 mol) was added at room temperature 30% NaOH to achieve approximately pH 8 (about 7.4 g of 30% NaOH). Then, to the resulting mixture was added isatoic anhydride in ten portions (total: 167.2 g, 0.974 mol, 95%) over a 3 h period. Before each addition of isatoic anhydride, the pH-value was readjusted with NaOH to about pH 8.5. The russet solution was heated for about 4 h until the coupling-reaction is finished. Without cooling, to the reaction was added a solution of L-tartaric acid (367.0 g, 2.445 mol) in water (367.0 g, 20.371 mol) to achieve approximately pH 3. The mixture was heated to reflux to redistill water (328.0 g). The distillation should not be interrupted, as there is a great risk that the reaction mixture could foam explosively. During this time, the benzodiazepine-dione product was already precipitating. To complete the cyclization, the suspension was heated for an additional 16 h, while monitoring its progression by HPLC. The mixture was allowed to cool to 50° C. before slowly adding NH₃ (250.0 g, 25% in water) to arrive at about pH 7.5. After cooling to room temperature, the suspension was stirred for 3 h to complete the precipitation. The beige colored precipitate was filtered, washed with NH₃ (100.0 g, 25% in water), water (300.0 g, 16.652 mol), and dried under vacuum at 80° C. for 8 h to afford the desired product (90.9 g, ee(R) 93%) as a beige powder.

B. 3S-Hydroxymethyl-2,3,4,5-tetrahydro-1,4-benzodiazepine. To a suspension of LAH (81.4 g, 2.144 mol) in THF (384.0 g) under refluxing conditions was added in portions a suspension of 3R-Hydroxymethyl-1,4-benzodiazepine-2,5-dione in THF (307 g) over a period of 1 h. After refluxing for about 20 h the yellow suspension was hydrolyzed by slowly and cautiously adding NaOH (129.5 g, 10%). The suspension was filtered at 30-40° C. and washed with a mixture of THF (5.0 g) and EtOH (15 g). The filtrate was collected, and residual aluminium salts were extracted under refluxing conditions in a mixture of THF (63 g) and EtOH (189 g) for 1 h. The mixture was filtered and washed with a mixture of THF (12.5 g) and EtOH (37.6 g). To remove the water, the combined filtrates were concentrated to an oil, and of IPA (60.0 g) was added two times and reduced in vacuo each time. The residue was dissolved in IPA (60.0 g) under reflux and cooled afterwards for crystallization at 0° C. for 15 h. The colorless crystals were filtered, washed with cold IPA and dried under vacuum to afford the product as colorless crystals (47.1 g, ee(S) 99.8%).

C. 3S-Hydroxymethyl-2,3,5-trihydro-4-tertbutyloxycarbonyl-1,4-benzodiazepine. To a stirred heterogeneous mixture of (5.1 g, 19.82 mmol) 3S-Hydroxymethyl-2,3,4,5-tetrahydro-1,4-benzodiazepine in water (40.0 g, 2.22 mol), EtOAc (40.0 g, 0.45 mol), and triethylamine (5.0 g, 49.51 mmol) was added Boc₂O (12.98 g, 59.47 mmol). The solution was refluxed for 4 h, and then stirred at room temperature overnight. After separating the phases, the organic phase was washed with 25% aqueous NH₃, dried over anhydrous MgSO₄, filtered, and reduced under vacuum. The microcrystalline residue was stirred in cold Et₂O (15.0 g) for 30 min. At that time the mixture was filtered, washed with a small amount of cold Et₂O, and dried under vacuum to afford the product (5.17 g) as a colorless microcrystalline powder.

D. 4-[[Biphenyl-2-carbonyl]-amino]-2-chlorobenzoic acid. A sample of 2-phenylbenzoic acid (11.56 g, 0.058 mol) was dissolved in toluene (103 g). The reaction mixture was cooled to 5° C. and a catalytic amount of DMF (0.103 g) was added. After 20 min of stirring at 5° C., oxalyl chloride (8.14 g, 0.064 mol) was added over a period of 30 min. The reaction mixture was stirred for 5 h until gas evolution ceased. The resulting solution was concentrated in vacuo to remove the excess of oxalyl chloride. After distillation, toluene (10.0 g) was added to the resultant residue, Cpd AA8.

A sample of 4-amino-2-chlorobenzoic acid (10.0 g, 0.058 mol) was suspended in toluene (100.0 g) at ambient temperature. Pyridine (25.38 g, 0.323 mol) was added to the suspension and the reaction mixture was stirred for 15 min. The suspension was cooled to 5° C. and TMSCI (17.43 g, 0.161 mol) was added. The reaction mixture was stirred for another 30 min at 5° C. followed by the slow addition of a solution of Cpd AA8 in toluene at temperatures below 10° C. After stirring for 2.5 h at 5° C., a mixture of concentrated hydrochloric acid (8.0 g, 0.219 mol, 37%), purified water (50.0 g), and ethanol (50.0 g) are added. The reaction was stirred for 15 min at 25° C. and the product began to crystallize. The reaction mixture was heated for 30 min to 85° C. and then slowly cooled to ambient temperature overnight. The slightly pink solids were filtered off and washed first with a mixture of purified water (25.0 g) and ethanol (25.0 g), then with 50.0 g of water purified. The filter cake was dried for 8 h at 80° C. in vacuo to yield the product (19.20 g, 94%) as a slightly pink solid.

E. 4-[[Biphenyl-2-carbonyl]-amino]-2-chlorobenzoic acid chloride. A sample of 4-[[biphenyl-2-carbonyl]-amino]-2-chlorobenzoic acid (19.0 g, 0.054 mol) was suspended in n-butyl acetate (55.0 g). Thionyl chloride (16.1 g, 0.135 mol) was added. The suspension was heated to 65° C., and gas formation was observed. After 2 h a slightly yellow solution was formed. The solution was concentrated at 50° C. in vacuo (10 mbar, distillate about 50 g) to remove the excess thionyl chloride. Acetonitrile (50.0 g) was added to the resulting oil.

F. (S)-Biphenyl-2-carboxylic acid [3-chloro-4-(3-hydroxymethyl-2,3,4,5-tetrahydrobenzo[e][1,4]diazepine-1-carbonyl)-phenyl]-amide. To a solution of Cpd AA6 (5.0 g, 17.96 mmol) and DIPEA (2.4 g, 18.57 mmol) in CH₂Cl₂ (63 g) at room temperature was added a solution of 4-[[biphenyl-2-carbonyl]-amino]-2-chlorobenzoic acid chloride (18.0 mmol) in CH₂Cl₂ (70 g). After stirring for 2.5 h, HCl (g) (excess) was introduced into the solution to afford a suspension which then became a brown oil. Water (60.0 g) was added to give a solution which was then stirred for 12 h at room temperature. To the mixture was added with 25% aqueous NH₃ to bring the mixture to pH 8.5. The phases of the mixture were separated, and the organic phase was washed with water, dried over anhydrous MgSO₄, and concentrated under vacuum to afford the crude product as its free base. Purification of the free base was performed by column chromatography (silica gel 60). The impurities were first eluted using EtOAc, followed by elution of the desired product with a mixture of MeOH/EtOAc (1:4). The fractions were concentrated to dryness under vacuum to afford a colorless oil which solidified with continuous drying (6.8 g as a colorless powder).

Example 1

(S)-Biphenyl-2-carboxylic acid [4-(4-benzyl-3-hydroxymethyl-2,3,4,5-tetrahydro-benzo[e][1,4]diazepine-1-carbonyl)-3-chloro-phenyl]-amide, Cpd 1

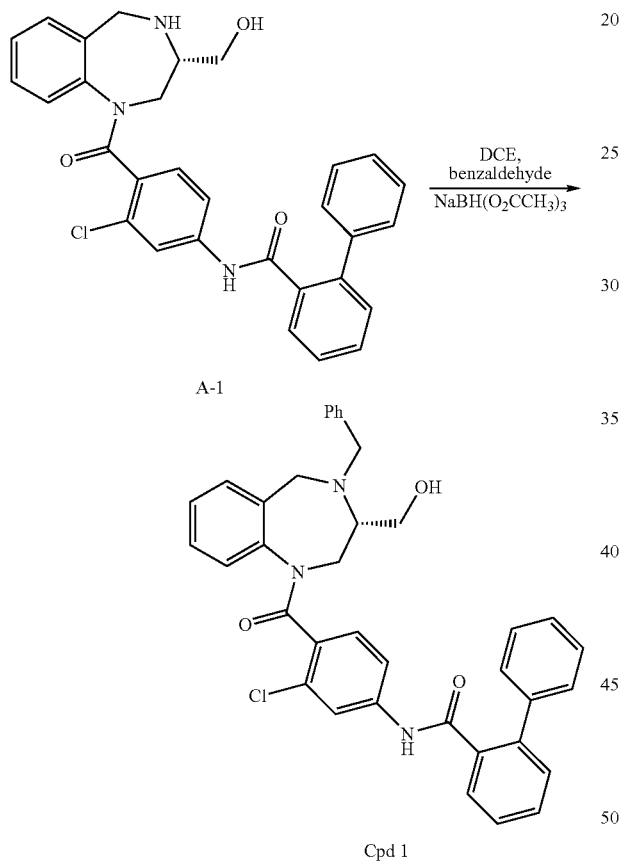

To a solution of (S)-biphenyl-2-carboxylic acid [3-chloro-4-(3-hydroxymethyl-2,3,4,5-tetrahydrobenzo[e][1,4]diazepine-1-carbonyl)-phenyl]-amide (1.02 g; 1.95 mmol) dissolved in ClCH₂CH₂Cl (11 mL) was added benzaldehyde (2.92 mmol) followed by sodium triacetoxyborohydride (0.824 g; 3.89 mmol) in one-portion and the reaction was stirred for 18 h at rt. The reaction was diluted with CH₂Cl₂, washed with H₂O, dried over Na₂SO₄, filtered, and the solvent removed under reduced pressure to afford a crude residue which was purified by flash chromatography (SiO₂) eluting with EtOAc-MeOH gradient to afford 0.949 g (81%) of the title compound as a white solid. $[\alpha]^{23}_D$: −75° (c 1.4, MeOH); ¹H NMR (300 MHz, CDCl₃): δ 7.81-7.83 (d, 1H), 7.28-7.56 (m, 13H), 6.71-7.20 (m, 7H), 4.77-4.82 (m, 1H), 4.40-4.46 (m, 1H), 3.85-4.10 (m, 2H), 3.52-3.69 (m, 3H), 3.31-3.36 (m, 1H), 3.14 (s, 1H); LC/MS m/z 602 (M+1). Calcd for C₃₃H₃₂ClN₃O₃·0.88% H₂O; C, 72.08; H, 5.31; N, 6.80; Cl, 6.91.

Example 2

(S)-Biphenyl-2-carboxylic acid [3-chloro-4-(4-methyl-3-methylsulfanylmethyl-2,3,4,5-tetrahydrobenzo[e][1,4]diazepine-1-carbonyl)-phenyl]-amide, Cpd 2

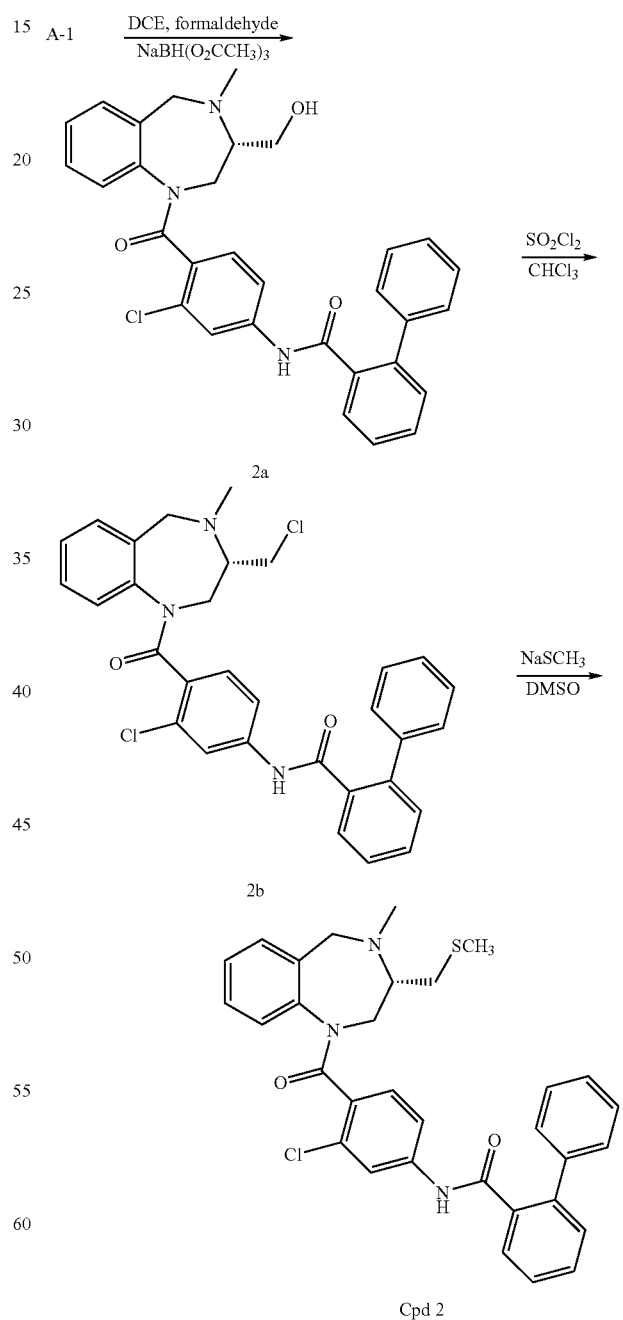

A. Biphenyl-2-carboxylic acid [3-chloro-4-(3-hydroxymethyl-4-methyl-2,3,4,5-tetrahydro-benzo[e][1,4]diazepine- 1-carbonyl)-phenyl]-amide. Compound A1 was converted to the Cpd 2b using the method described in Example 1, substituting formaldehyde for benzaldehyde.

B. (S)-Biphenyl-2-carboxylic acid [3-chloro-4-(3-chloromethyl-4-methyl-2,3,4,5-tetrahydrobenzo[e][1,4]diazepine-1-carbonyl)-phenyl]-amide. To a solution of Compound 2a (0.67 g; 1.27 mmol) dissolved in CHCl$_3$ (4 mL) was added thionyl chloride (0.185 μL; 2.53 mmol) in one-portion and the reaction was stirred for 18 h at 60° C. The reaction was cooled, the solvent removed in vacuo, and the crude residue was purified by flash chromatography (SiO$_2$) eluting with a CH$_2$Cl$_2$-MeOH (1% NH$_4$OH) gradient to afford 0.621 g (90%) of Cpd 2b as a white solid. LC/MS m/z 544 (M+1).

C. (S)-Biphenyl-2-carboxylic acid [3-chloro-4-(4-methyl-3-methylsulfanylmethyl-2,3,4,5-tetrahydrobenzo[e][1,4]diazepine-1-carbonyl)-phenyl]-amide, Cpd 2. A pressure vessel was charged with a solution of (S)-biphenyl-2-carboxylic acid [3-chloro-4-(3-chloromethyl-4-methyl-2,3,4,5-tetrahydrobenzo-[e][1,4]diazepine-1-carbonyl)-phenyl]-amide (0.2 g; 0.38 mmol) dissolved in (CH$_3$)$_2$SO (2 mL) followed by the addition of sodium thiomethoxide (0.158 g; 2.25 mmol) in one-portion and the reaction was sealed and stirred for 18 h at 90° C. The reaction was cooled, diluted with EtOAc, washed with H$_2$O (2×), brine, dried over Na$_2$SO$_4$, filtered, and the solvent removed under reduced pressure to afford a crude residue, which was purified by flash chromatography (SiO$_2$) eluting with heptane-EtOAc gradient to afford 0.092 g (44%) of the title compound, Cpd 2, as a white solid. $[\alpha]^{23}_D$ +14° (c 0.36, MeOH); $^1$H NMR (500 MHz, CD$_3$OD): δ 7.20-7.60 (m, 10H), 6.87-7.15 (m, 4H), 4.43-4.57 (m, 1H), 3.87 (m, 1H), 3.31-3.53 (m, 1H), 2.72-2.98 (m, 2H), 2.47-2.58 (m, 2H), 2.17-2.35 (m, 6H); LC/MS m/z 556 (M+1).

Following the procedure described above for Example 2 and substituting the appropriate reagents, starting materials and purification methods known to those skilled in the art, the following compounds of the present invention were prepared:

| Cpd | Compound name | MS(obs) |
|---|---|---|
| 3 | (S)-Biphenyl-2-carboxylic acid [3-chloro-4-(4-methyl-3-pyrrolidin-1-ylmethyl-2,3,4,5-tetrahydrobenzo[e][1,4]diazepine-1-carbonyl)-phenyl]amide ditrifluoroacetate | 579.9 |
| 4 | (S)-Biphenyl-2-carboxylic acid [3-chloro-4-(3-cyclopentyloxymethyl-4-methyl-2,3,4,5-tetrahydrobenzo[e][1,4]diazepine-1-carbonyl)-phenyl]-amide trifluoroacetate | 593.8 |
| 5 | S)-Biphenyl-2-carboxylic acid [3-chloro-4-(4-methyl-3-morpholino-4-ylmethyl-2,3,4,5-tetrahydrobenzo[e][1,4]diazepine-1-carbonyl)-phenyl]-amide ditrifluoroacetate | 594.8 |
| 6 | (S)-Biphenyl-2-carboxylic acid [3-chloro-4-(3-methoxymethyl-4-methyl-2,3,4,5-tetrahydrobenzo[e][1,4]diazepine-1-carbonyl)-phenyl]-amide trifluoroacetate | 539.8 |

Cpd 3: Compound 3 was prepared following Example 2 and replacing sodium thiomethoxide and (CH$_3$)$_2$SO with pyrrolidine and toluene, respectively, and the reaction was heated at 110° C. for 18 h and purified by reverse-phase semi-prep HPLC. $[\alpha]^{23}_D$ –62.70 (c 0.667, MeOH); $^1$H NMR (500 MHz, CD$_3$OD): δ 7.55-7.58 (m, 3H), 7.44-7.53 (m, 2H), 7.36-7.39 (m, 2H), 7.23-7.34 (m, 4H), 7.17-7.19 (t, 3H), 7.06-7.12 (t, 3H), 6.90-6.91 (d, 1H), 4.64-4.67 (d, 1H), 3.32-3.92 (m, 7H), 3.17-3.29 (m, 2H), 2.37 (s, 3H), 1.98-2.09 (m, 3H); LC/MS m/z 579.9 (M+1). Calcd for C$_{35}$H$_{35}$ClN$_4$O$_2$.2.2C$_2$HF$_3$O$_2$; C, 57.11; H, 4.13; N, 6.63; Cl, 4.14.

Cpd 4: Compound 4 was prepared following Example 2 and replacing sodium thiomethoxide and (CH$_3$)$_2$SO with sodium cyclopentoxide and toluene, respectively, and the reaction was heated at 110° C. for 18 h and purified by reverse-phase semi-prep HPLC. $[\alpha]^{23}_D$ +50.70 (c 0.693, MeOH); $^1$H NMR (500 MHz, CD$_3$OD): δ 7.00-7.65 (m, 13H), 7.25-7.26 (m, 2H), 7.00-7.15 (m, 1H), 3.89-4.06 (m, 4H), 2.78 (bs, 3H), 1.58-1.72 (m, 6H); LC/MS m/z 593.8 (M+).

Cpd 5: Compound 5 was prepared following Example 2 and replacing sodium thiomethoxide and (CH$_3$)$_2$SO with morpholine and toluene, respectively, and the reaction was heated at 110° C. for 5 h and purified by reverse-phase semi-prep HPLC. $[\alpha]^{23}_D$ –9.1° (c 0.753, MeOH); $^1$H NMR (500 MHz, CD$_3$OD): δ 7.57-7.47 (m, 5H), 7.45-7.29 (m, 2H), 7.30-6.90 (m, 9H), 4.70-4.78 (m, 1H), 4.24-4.68 (m, 1H), 3.86-4.11 (m, 4H), 3.49-3.74 (m, 3H), 3.26-3.44 (m, 2H), 2.85-3.16 (m, 2H), 2.37-2.43 (s, 3H); LC/MS m/z 594.8 (M+). Calcd for C$_{35}$H$_{35}$ClN$_4$O$_3$.2C$_2$HF$_3$O$_2$; C, 55.84; H, 4.13; N, 6.38; Cl, 5.29.

Cpd 6: Compound 6 was prepared following Scheme 1, Step C by replacing sodium thiomethoxide and (CH$_3$)$_2$SO with sodium methoxide and MeOH, respectively and the reaction was heated at 65° C. for 16 h and purified by reverse-phase semi-prep HPLC. $[\alpha]^{23}_D$ +49.2° (c 0.433, MeOH); $^1$H NMR (300 MHz, CD$_3$OD): δ 7.01-7.76 (m, 16H), 3.31-4.79 (m, 10H), 2.79-3.29 (m, 3H); LC/MS m/z 539.8 (M+). Calcd for C$_{32}$H$_{30}$ClN$_3$O$_3$.C$_2$HF$_3$O$_2$; C, 57.82; H, 4.63; N, 5.76; Cl, 4.86.

Example 3

(S)-Biphenyl-2-carboxylic acid [3-chloro-4-(3-hydroxymethyl-4-methanesulfonyl-2,3,4,5-tetrahydrobenzo[e][1,4]diazepine-1-carbonyl)-phenyl]-amide, Cpd 7 and (S)-methanesulfonic acid 1 {4-[(biphenyl-2-carbonyl)-amino]-2chloro-benzoyl}-4-methanesulfonyl-2,3,4,5-tetrahydro-1H-benzo[e][1,4]diazepin-3-ylmethyl ester, Cpd 8

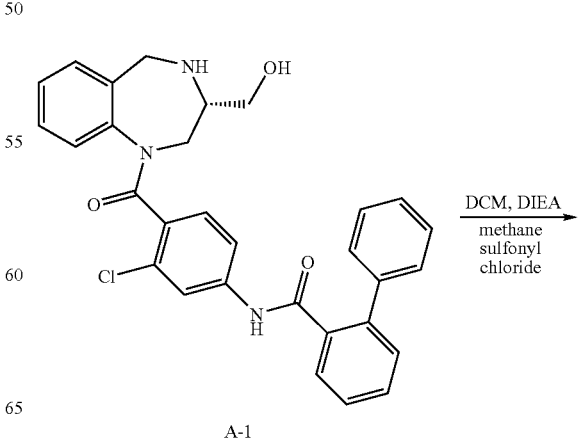

A-1

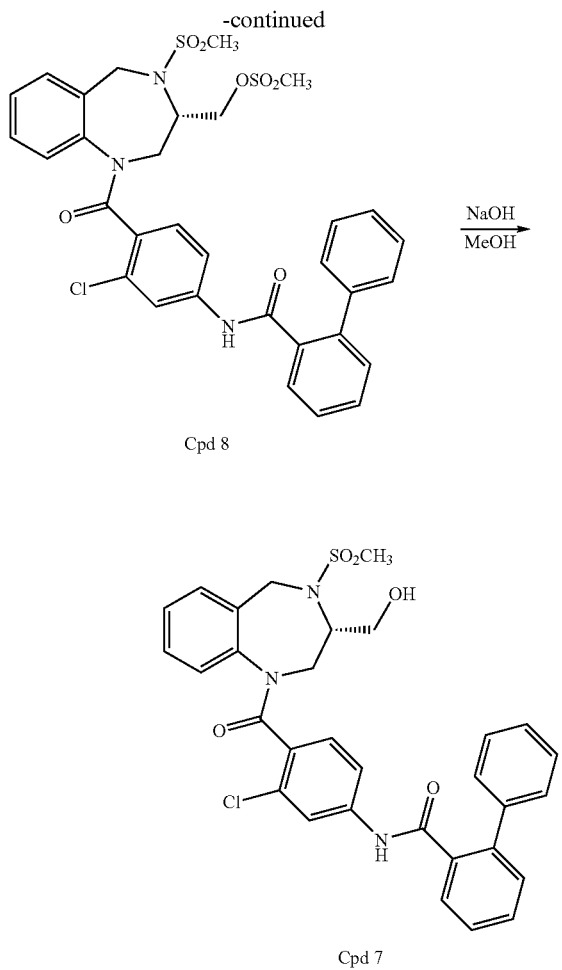

Cpd 8

Cpd 7

To a solution of Compound A-1 of Example M (0.257 g; 0.502 mmol) dissolved in $CH_2Cl_2$ (5 mL) was added diisopropylethylamine (0.105 mL; 0.602 mmol). The reaction was cooled to 0° C., methanesulfonyl chloride (0.058 mL; 0.911 mmol) was added dropwise, allowed to warm to ambient temperature and stirred for 2 h. The reaction was diluted with $CH_2Cl_2$, washed with $H_2O$, dried over $Na_2SO_4$, filtered, and the solvent removed under reduced pressure to afford a crude mixture of Cpd 7 and Cpd 8. The compounds were separated by reverse-phase semi-prep HPLC to afford 0.158 g (53%) of Cpd 7 as a white solid and 0.047 g (16%) of Cpd 8 as a white solid. Cpd 7: $[\alpha]^{23}_D$ +123° (c 0.866, MeOH); $^1$H NMR (300 MHz, $CDCl_3$): δ 7.06-7.58 (m, 16H), 5.16-5.21 (m, 1H), 4.80-4.45 (m, 4H), 4.13 (m, 1H), 3.04-3.29 (m, 4H), 2.68 (s, 1H); LC/MS m/z 590 (M+1). Calcd for $C_{31}H_{28}ClN_3O_5S$; C, 55.51; H, 3.98; N, 5.78; Cl, 5.17; S, 5.17.

Cpd 8: $[\alpha]^{23}_D$ −90° (c 0.680, MeOH); $^1$H NMR (300 MHz, $CDCl_3$): δ 7.19-7.58 (m, 16H), 4.59-4.79 (m, 5H), 3.25-3.29 (m, 5H), 3.18 (s, 3H); LC/MS m/z 668 (M+1). Calcd for $C_{32}H_{30}ClN_3O_7S_2$; C, 56.27; H, 4.14; N, 6.17; Cl, 4.96; S, 9.03.

Following the procedure described above for Example 3 and substituting the appropriate reagents, starting materials and purification methods known to those skilled in the art, the following compounds of the present invention were prepared:

| Cpd | Compound name | MS(obs) |
|---|---|---|
| 9 | (S)-Acetic acid 4-acetyl-1-{4-[(biphenyl-2-carbonyl)-amino]-2-chloro-benzoyl}-2,3,4,5-tetrahydro-1H-benzo[e][1,4]diazepin-3-ylmethyl ester | 554.2 |
| 10 | (S)-Biphenyl-2-carboxylic acid {3-chloro-4-[3-hydroxymethyl-4-(propane-1-sulfonyl)-2,3,4,5-tetrahydrobenzo[e][1,4]diazepine-1-carbonyl]-phenyl}-amide | 617.7 |
| 11 | (S)-Biphenyl-2-carboxylic acid [4-(4-benzenesulfonyl-3-hydroxymethyl-2,3,4,5-tetrahydrobenzo[e][1,4]diazepine-1-carbonyl)-3-chloro-phenyl]-amide | 651.8 |
| 12 | (S)-Biphenyl-2-carboxylic acid [4-(4-acetyl-3-hydroxymethyl-2,3,4,5-tetrahydro-benzo[e][1,4]diazepine-1-carbonyl)-3-chloro-phenyl]-amide | 554.2 |

Cpd 9: Compound 9 was prepared following Example 3 and replacing methanesulfonyl chloride with acetyl chloride. $[\alpha]^{23}_D$ +14° (c 0.360, MeOH); $^1$H NMR (300 MHz, $CD_3OD$): δ 6.90-7.58 (m, 16H), 4.93-5.36 (m, 2H), 4.43-4.80 (m, 5H), 1.98-2.20 (m, 6H); LC/MS m/z 554.2 (M-$CO_2CH_3$). Calcd for $C_{34}H_{30}ClN_3O_5 \cdot 0.1H_2O$; C, 64.61; H, 4.65; N, 6.44; Cl, 5.38.

Cpd 10: Compound 10 was prepared following Example 3 and replacing methanesulfonyl chloride with 1-propanesulfonyl chloride. $[\alpha]^{23}_D$ +87.1° (c 1.02, MeOH); $^1$H NMR (300 MHz, $CDCl_3$): δ 7.82-7.84 (d, 1H), 7.09-7.58 (m, 11H), 6.69-6.88 (m, 4H), 5.08-5.13 (d, 1H), 4.44-4.65 (m, 5H), 3.96 (s, 1H), 3.18-3.28 (m, 3H), 1.89-1.91 (m, 2H), 1.04-1.09 (t, 3H); LC/MS m/z 617.7 (M+). Calcd for $C_{33}H_{32}ClN_3O_5S \cdot 0.7\% H_2O$; C, 56.04; H, 4.23; N, 5.34; Cl, 4.78; S, 4.68.

Cpd 11: Compound 11 was prepared following Example 3 and replacing methanesulfonyl chloride with benzenesulfonyl chloride. $[\alpha]^{23}_D$ −88.3° (c 0.526, MeOH); $^1$H NMR (300 MHz, $CDCl_3$): δ 7.82-7.84 (d, 1H), 7.18-7.68 (m, 15H), 6.68-7.15 (m, 5H), 4.85-4.95 (m, 2H), 4.53-4.80 (d, 1H), 4.18 (m, 1H), 3.66-4.03 (m, 5H), 3.60-3.64 (m, 1H), 2.79-2.83 (d, 1H); LC/MS m/z 651.8 (M+). Calcd for $C_{36}H_{30}ClN_3O_5S \cdot 0.3\% H_2O$; C, 63.94; H, 4.15; N, 6.01; Cl, 5.16; S, 4.90.

Cpd 12: Using the method described for the conversion of Compound 8 to Compound 7, Compound 9 was converted to Compound 12. To a solution of Cpd 9 (0.2 g; 0.4 mmol) dissolved in MeOH (5 mL) was added 1N $NaOH_{aq}$ (0.5 mL; 0.5 mmol). The reaction was stirred at ambient temperature for 15 min and subsequently purified by reverse-phase semi-prep HPLC to afford 0.110 g (49%) of Cpd 12 as a white solid: $[\alpha]^{23}_D$ +34° (c 0.760, MeOH); $^1$H NMR (300 MHz, $CDCl_3$): δ 7.19-7.58 (m, 16H), 4.59-4.79 (m, 5H), 3.25-3.29 (m, 5H), 3.18 (s, 3H); LC/MS m/z 554.2 (M+1). Calcd for $C_{32}H_{28}ClN_3O_4$; C, 63.04; H, 4.45; N, 6.66; Cl, 5.69.

The compounds of Formula (I) may be prepared by an alternative synthetic route, as illustrated below.

Example BB

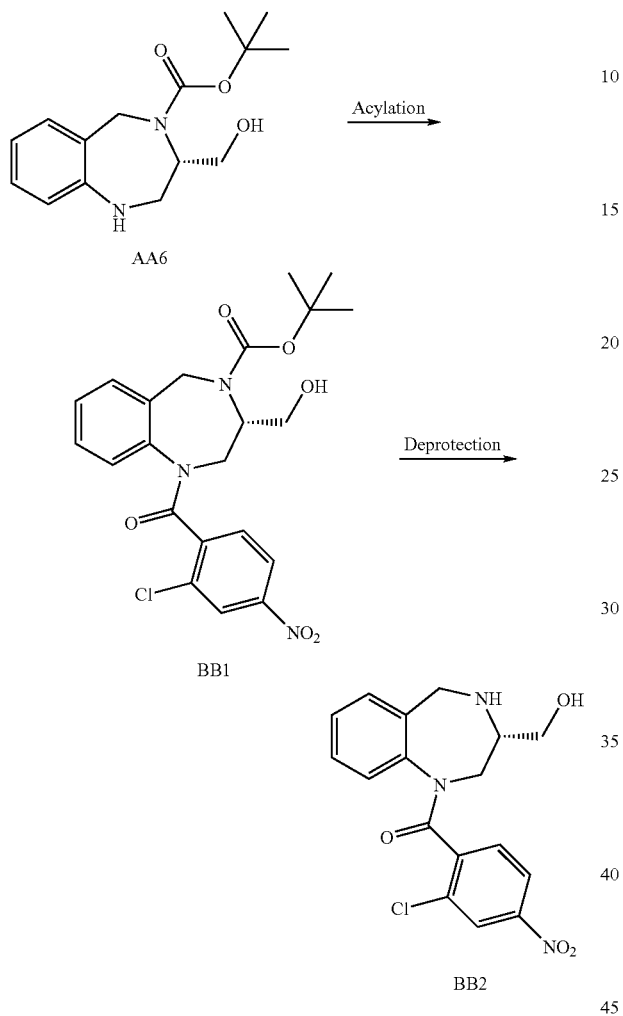

A. 1-(2-Chloro-4-nitro-benzoyl)-3-hydroxymethyl-2,3,4,5-tetrahydro-benzo[e][1,4]diazepine-4-carboxylic acid tert-butyl ester. To a solution of Cpd AA6 in CH$_2$Cl$_2$ may be added DIEA (1.3 equiv) and the reaction may be cooled to 0° C. A portion of 2-chloro-4-nitrobenzoyl chloride (1.1 equiv) may be added dropwise while maintaining the temperature at 0° C. The reaction may be allowed to warm to ambient temperature and the reaction stirred until completion. At that time, the reaction may be diluted with CH$_2$Cl$_2$, washed with H$_2$O, dried over Na$_2$SO$_4$, and filtered. The filtrate may be concentrated under reduced pressure and the resultant residue may be purified by flash chromatography (SiO$_2$), using a heptane-EtOAc gradient to afford Cpd BB1.

B. (2-Chloro-4-nitro-phenyl)-(3-hydroxymethyl-2,3,4,5-tetrahydro-benzo[e][1,4]diazepin-1-yl)-methanone. To a solution of Cpd BB1 in EtOAc cooled to 0° C. may be bubbled HCl (g) for 15 min and the reaction stirred until completion. The solvent may be evaporated under reduced pressure and the resultant residue may be triturated with ether, filtered, and then dried under reduced pressure to afford Cpd BB2 as its hydrochloride salt.

Example 4

(S)-Biphenyl-2-carboxylic acid [4-(4-benzyl-3-hydroxymethyl-2,3,4,5-tetrahydro-benzo[e][1,4]diazepine-1-carbonyl)-3-chloro-phenyl]-amide, Cpd 1

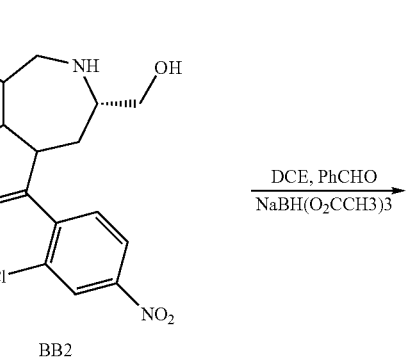

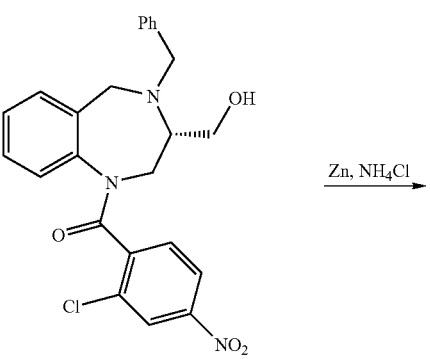

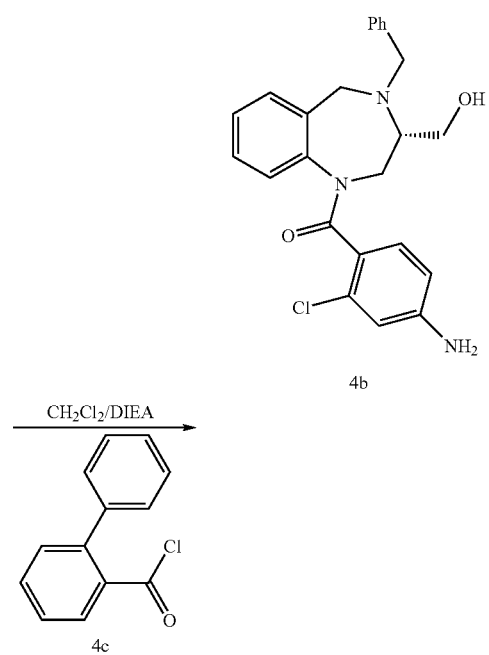

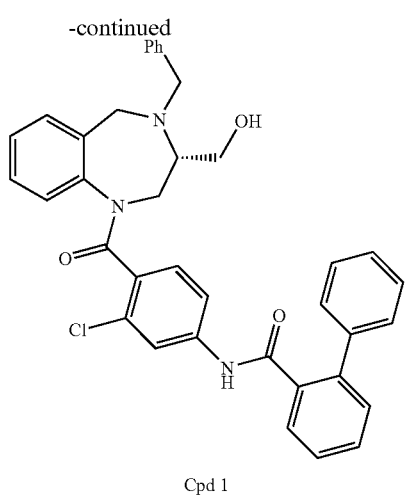

Cpd 1

A. (4-Benzyl-3-hydroxymethyl-2,3,4,5-tetrahydro-benzo[e][1,4]diazepin-1-yl)-(2-chloro-4-nitro-phenyl)-methanone. To a solution of Cpd BB2 dissolved in ClCH$_2$CH$_2$Cl may be added DIEA (1.1 equiv) and benzaldehyde (3.0 equiv) followed by sodium triacetoxyborohydride (2 equiv) in one portion. The reaction is stirred at rt until completion. The reaction may be diluted with CH$_2$Cl$_2$, washed with H$_2$O, dried over Na$_2$SO$_4$, filtered, and the solvent removed under reduced pressure to afford a crude residue, which may be purified by flash chromatography (SiO$_2$), eluting with a heptane-EtOAc gradient to afford the Cpd 4a.

B. (4-Amino-2-chloro-phenyl)-(4-benzyl-3-hydroxymethyl-2,3,4,5-tetrahydro-benzo[e][1,4]diazepin-1-yl)-methanone. To a solution of (4-benzyl-3-hydroxymethyl-2,3,4,5-tetrahydrobenzo[e][1,4]diazepin-1-yl)-(2-chloro-4-nitro-phenyl)-methanone dissolved in methanol may be added Zn dust (34 equiv) and ammonium chloride (16 equiv) and the reaction may be stirred at 65° C. until completion. The reaction may be filtered, the solvent removed under reduced pressure, the residue partitioned between EtOAc and 1N NaOH, separated, and the organic phase washed with H$_2$O, brine, and dried over Na$_2$SO$_4$. The solvent may be filtered and evaporated under reduced pressure to afford Cpd 4b.

C. (S)-Biphenyl-2-carboxylic acid [4-(4-benzyl-3-hydroxymethyl-2,3,4,5-tetrahydrobenzo[e][1,4]diazepine-1-carbonyl)-3-chloro-phenyl]-amide, Cpd 1. To a solution of (4-amino-2-chloro-phenyl)-(4-benzyl-3-hydroxymethyl-2,3,4,5-tetrahydrobenzo[e][1,4]diazpin-1-yl)-methanone in CH$_2$Cl$_2$ may be added DIEA (1.3 equiv) and the reaction may be cooled to 0° C. Biphenyl-2-carbonyl chloride (1.2 equiv) may be added dropwise while maintaining the temperature at 0° C. The reaction may be allowed to warm to ambient temperature and stirred until completion. The reaction may be diluted with CH$_2$Cl$_2$, washed with H$_2$O, dried over Na$_2$SO$_4$, filtered, and the solvent may be removed under reduced pressure. The crude residue may be purified by flash chromatography (SiO$_2$), eluting with a heptane-EtOAc gradient to afford a mixture of the title compound and a bis-acylated by-product. This mixture may be dissolved in methanol, and 1N NaOH (1.5 equiv) may be added and the solution stirred at 65° C. until completion. The reaction may be cooled, the solvent evaporated under reduced pressure, the residue dissolved in H$_2$O and acidified with 1N HCl. The resultant residue may be washed with H$_2$O and dried under vacuum to afford the title compound as a white solid.

Example 5

(S)-Biphenyl-2-carboxylic acid [3-chloro-4-(4-methyl-3-methylsulfanylmethyl-2,3,4,5-tetrahydrobenzo[e][1,4]diazepine-1-carbonyl)-phenyl]-amide, Cpd 2

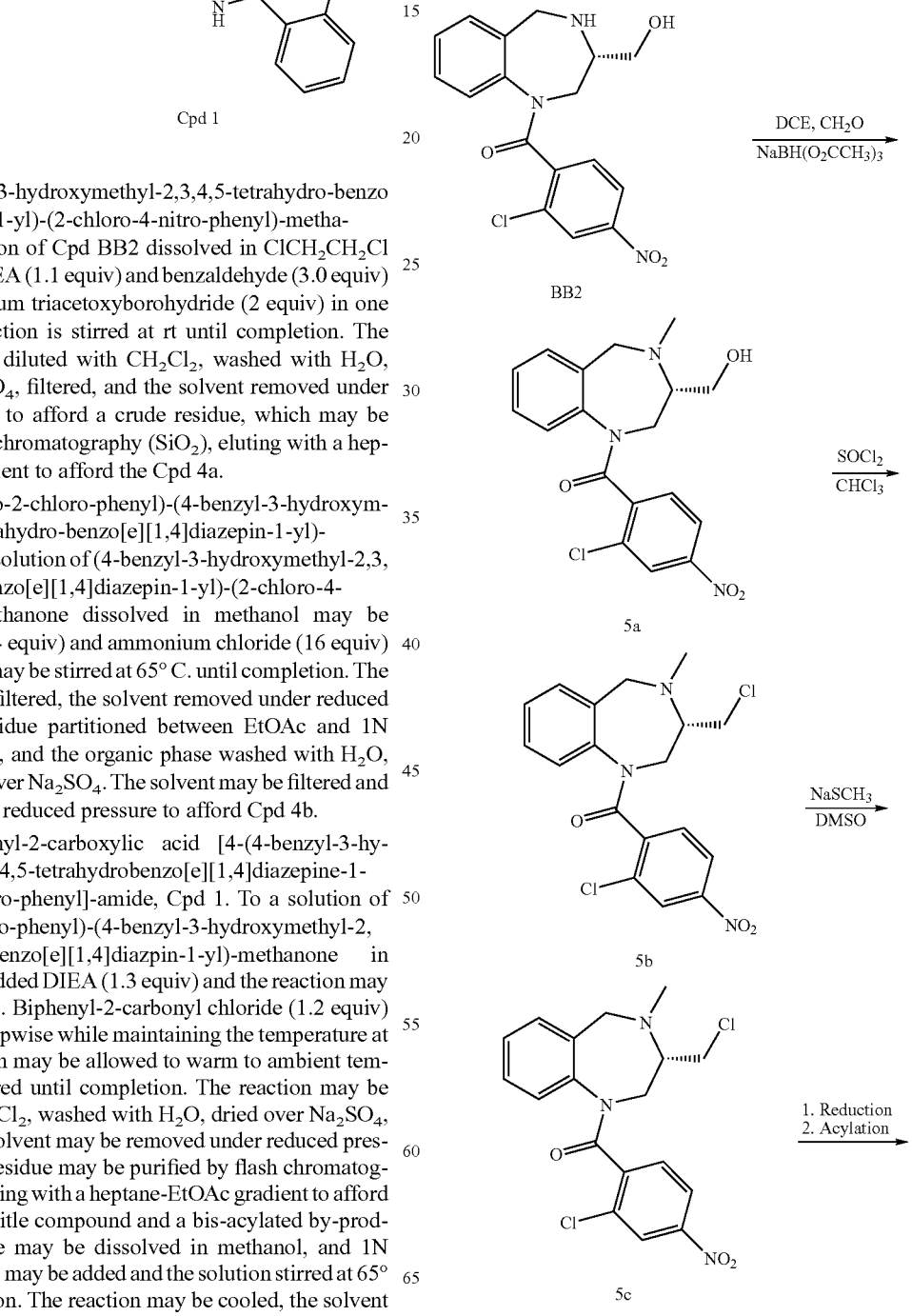

-continued

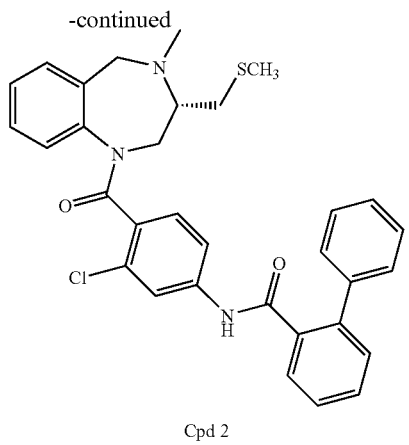

Cpd 2

A. (2-Chloro-4-nitro-phenyl)-(3-hydroxymethyl-4-methyl-2,3,4,5-tetrahydro-benzo[e][1,4]diazepin-1-yl)-methanone. To a solution of Cpd BB2 dissolved in ClCH$_2$CH$_2$Cl may be added DIEA (1.1 equiv) and 30% formaldehyde (3.0 equiv) followed by sodium triacetoxyborohydride (2 equiv) in one-portion and the reaction may be stirred at rt until completion. The reaction may be diluted with CH$_2$Cl$_2$, washed with H$_2$O, dried over Na$_2$SO$_4$, filtered, and the solvent may be removed under reduced pressure to afford a crude residue, which is purified by flash chromatography (SiO$_2$) eluting with a heptane-EtOAc gradient to afford Cpd 5a.

B. (3-Chloromethyl-4-methyl-2,3,4,5-tetrahydro-benzo[e][1,4]diazepin-1-yl)-(2-chloro-4-nitro-phenyl)-methanone. To a solution of 2-chloro-4-nitro-phenyl)-(3-hydroxymethyl-4-methyl-2,3,4,5-tetrahydro-benzo[e][1,4]diazepin-1-yl)-methanone dissolved in CHCl$_3$ may be added thionyl chloride (2.0 equiv) in one-portion. The reaction may be stirred at 60° C. until completion. The reaction may be cooled, the solvent removed in vacuo, and the crude residue may be purified by flash chromatography (SiO$_2$) eluting with a CH$_2$Cl$_2$-MeOH (1% NH$_4$OH) gradient to afford Cpd 5b.

C. (2-Chloro-4-nitro-phenyl)-(4-methyl-3-methylsulfanylmethyl-2,3,4,5-tetrahydro-benzo[e][1,4]diazepin-1-yl)-methanone. A pressure vessel may be charged with a solution of (3-chloromethyl-4-methyl-2,3,4,5-tetrahydro-benzo[e][1,4]diazepin-1-yl)-(2-chloro-4-nitro-phenyl)-methanone in DMSO. Sodium thiomethoxide (6 equiv) may be added to the mixture in one-portion, and the reaction may be sealed and stirred at 90° C. until completion. The reaction may be cooled to room temperature, diluted with EtOAc, washed sequentially with H$_2$O (2×), then brine, and the organic phase may be dried over Na$_2$SO$_4$. Upon filteration, the filtrate may be concentrated under reduced pressure to afford a crude residue, which may be purified by flash chromatography (SiO$_2$), eluting with a heptane-EtOAc gradient to afford Cpd 5c.

D. (4-Amino-2-chloro-phenyl)-(3-chloromethyl-4-methyl-2,3,4,5-tetrahydro-benzo[e][1,4]diazepin-1-yl)-methanone. The title compound may be prepared using an adaptation of Step B of Example 4, and replacing (4-benzyl-3-hydroxymethyl-2,3,4,5-tetrahydrobenzo[e][1,4]diazepin-1-yl)-(2-chloro-4-nitro-phenyl)-methanone with Cpd 5c.

E. Biphenyl-2-carbocylic acid-[3-Chloro-4-(4-methyl-3-methylsulfanylmethyl-2,3,4,5-tetrahydro-benzo[e][1,4]diazepine-1-carbonyl)-phenyl]-amide. The title compound 2 may be prepared from Cpd 5c using the methods described in Step C of Example 4.

Example 6

(S)-Biphenyl-2-carboxylic acid [3-chloro-4-(4-methyl-3-pyrrolidin-1-ylmethyl-2,3,4,5-tetrahydrobenzo[e][1,4]diazepine-1-carbonyl)-phenyl]-amide ditrifluoroacetate, Cpd 3

The title compound may be prepared using the methods described in Step C of Example 5, replacing sodium thiomethoxide with pyrrolidine, and replacing DMSO with toluene. The reaction may be stirred and heated at 110° C. until the reaction has gone to completion. The resultant residue may be purified by reverse-phase semi-prep HPLC.

Example 7

(S)-Biphenyl-2-carboxylic acid [3-chloro-4-(3-cyclopentyloxymethyl-4-methyl-2,3,4,5-tetrahydrobenzo[e][1,4]diazepine-1-carbonyl)-phenyl]-amide trifluoroacetate, Cpd 4

The title compound may be prepared using the methods described in Step C of Example 5, replacing sodium thiomethoxide with sodium cyclopentoxide, and replacing DMSO with toluene. The reaction may be stirred and heated at 110° C. until the reaction has gone to completion. The resultant residue may be purified by reverse-phase semi-prep HPLC.

Example 8

(S)-Biphenyl-2-carboxylic acid [3-chloro-4-(4-methyl-3-morpholino-4-ylmethyl-2,3,4,5-tetrahydrobenzo[e][1,4]diazepine-1-carbonyl)-phenyl]-amide ditrifluoroacetate, Cpd 5

The title compound may be prepared using the methods described in Step C of Example 5, replacing sodium thiomethoxide with morpholine, and replacing DMSO with toluene. The reaction may be stirred and heated at 110° C. until the reaction has gone to completion. The resultant residue may be purified by reverse-phase semi-prep HPLC.

Example 9

(S)-Biphenyl-2-carboxylic acid [3-chloro-4-(3-methoxymethyl-4-methyl-2,3,4,5-tetrahydrobenzo[e][1,4]diazepine-1-carbonyl)-phenyl]-amide trifluoroacetate, Cpd 6

The title compound may be prepared using the methods described in Step C of Example 5, replacing sodium thiomethoxide with sodium methoxide, and replacing DMSO with toluene. The reaction may be stirred and heated at 110° C. until the reaction has gone to completion. The resultant residue may be purified by reverse-phase semi-prep HPLC.

Example 10

(S)-Methanesulfonic acid 1-{4-[(biphenyl-2-carbonyl)-amino]-2chloro-benzoyl}-4-methanesulfonyl-2,3,4,5-tetrahydro-1H-benzo[e][1,4]diazepin-3-ylmethyl ester, Cpd 7 and (S)-Biphenyl-2-carboxylic acid [3-chloro-4-(3-hydroxymethyl-4-methanesulfonyl-2,3,4,5-tetrahydrobenzo[e][1,4]diazepine-1-carbonyl)-phenyl]-amide, Cpd 8

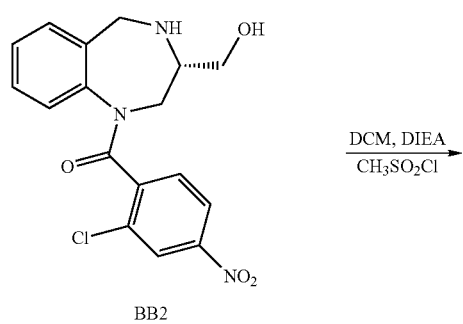

BB2

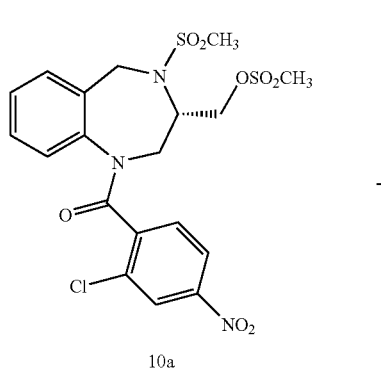

10a

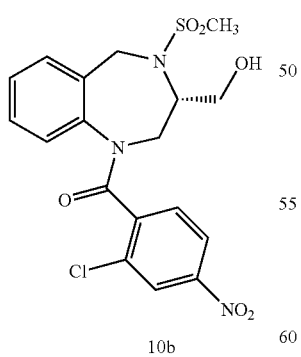

10b

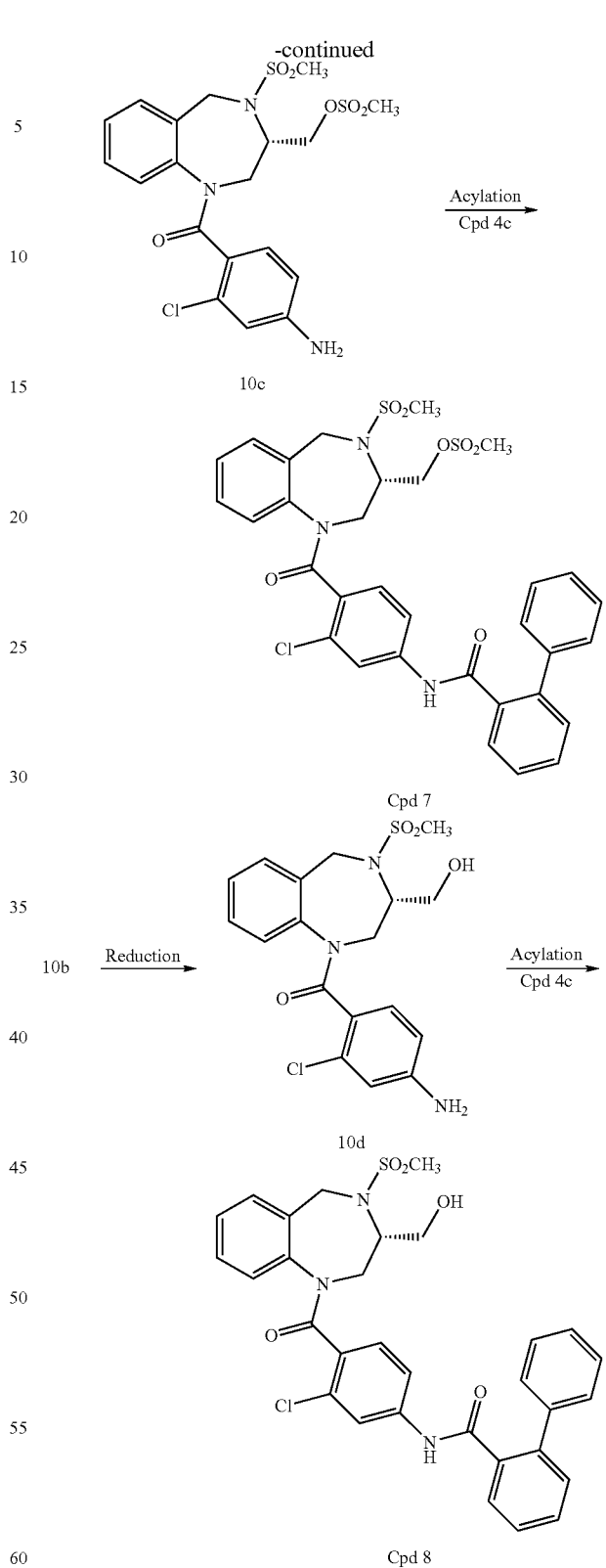

A. Compound BB2 of Example 4 may be dissolved in CH$_2$Cl$_2$ (5 mL) and diisopropylethylamine (1 equiv) may be added. The reaction may be cooled to 0° C., and methanesulfonyl chloride (1.5 equiv) may be added dropwise, allowed to warm to ambient temperature and stirred until completion.

The reaction may be diluted with $CH_2Cl_2$, washed with $H_2O$, dried over $Na_2SO_4$, filtered, and the solvent may be removed under reduced pressure to afford a mixture of Cpd 10a and Cpd 10b. The compounds may be separated by reverse-phase semi-prep HPLC.

B. Compounds 10a and Compound 10b may be converted to Compounds 10c and Compound 10d, respectively, using the methods described in Step B of Example 4.

C. Compounds 10c and Compound 10d may be converted to Compounds 7 and Compound 8, respectively, using the methods described in Step C of Example 4.

Example 11

(S)-Acetic acid 4-acetyl-1-{4-[(biphenyl-2-carbonyl)-amino]-2-chloro-benzoyl}-2,3,4,5-tetrahydro-1H-benzo[e][1,4]diazepin-3-ylmethyl ester, Cpd 9 and (S)-Biphenyl-2-carboxylic acid [4-(4-acetyl-3-hydroxymethyl-2,3,4,5-tetrahydro-benzo[e][1,4]diazepine-1-carbonyl)-3-chloro-phenyl]-amide, Cpd 12

The title compounds may be prepared using the methods described in Example 10, substituting acetyl chloride for methanesulfonyl chloride in Step A.

Example 12

(S)-Biphenyl-2-carboxylic acid {3-chloro-4-[3-hydroxymethyl-4-(propane-1-sulfonyl)-2,3,4,5-tetrahydrobenzo[e][1,4]diazepine-1-carbonyl]-phenyl}-amide, Cpd 10

The title compound may be prepared using the methods described in Example 10, substituting propanesulfonyl chloride for methanesulfonyl chloride in Step A.

Example 13

(S)-Biphenyl-2-carboxylic acid [4-(4-benzenesulfonyl-3-hydroxymethyl-2,3,4,5-tetrahydrobenzo[e][1,4]diazepine-1-carbonyl)-3-chloro-phenyl]-amide, Cpd 11

The title compound may be prepared using the methods described in Example 10, substituting benzenesulfonyl chloride for methanesulfonyl chloride in Step A.

Biological Examples

In vitro Recombinant Vasopressin Receptor Binding Assay

Compounds were assessed for their ability to displace $^3$H-arginine vasopressin from the human V-1 or V-2 receptor in HEK-293 cells. Assay buffer is 50 mM Tris-Cl, 5 mM $MgCl_2$, 0.1% BSA (pH 7.5) containing 5 ug/ml of aprotinin, leupeptin, pepstatin, 50 ug/ml bacitracin, and 1 mM Pefabloc. $^3$H-vasopressin is $^3$H-arginine-8-vasopressin (68.5 Ci/mmol, final concentration in assay is 0.65-0.75 nM). Into wells of 96-well round bottom polypropylene plates were added buffer, test compound, membrane (containing cloned human V-1 or V-2 receptor), and $^3$H-vasopressin. The reaction plates were allowed to sit at room temperature for one hour. The samples were filtered through Unifilter GF/C plates (presoaked in 0.3 polyethyleneimine). The plates were washed 5 times with cold physiological saline containing 0.05% Tween 20. After drying, the bottom of the filter plates were sealed and 0.025 ml of Microscint-20 was added to each filter. The top of the plate was sealed, and the plate was counted. Nonspecific binding was determined by the addition of 1.25 uM arginine-8-vasopressin in those wells.

Inhibition of AVP-Induced Effects in Human Vasopressin Receptors

HEK-293 cells were grown in DMEM media supplemented with 10% FBS and glutamine (Gibco BRL, Grand Island, N.Y.). Once transfected, the cells were passed biweekly by trypsinization and seeded into 96 well plates at 33,000 cells per well. HEK-293 were transfected with human V1a, V1b or V2 DNA using DMRIE-C reagent from Life Technologies, Inc., Grand Island, N.Y. Cells were tested for their responsiveness to vasopressin 48 h after transfection. Stable lines were generated by selecting cells grown in culture media containing geneticin (500 μg/mL, Life Technologies).

The accumulation of cAMP was measured in transfected HEK-293 expressing the human V2 receptor. The cells were cultured 4-7 d in 96-well plates. On the day of testing in this assay, cells were washed twice in assay media (DMEM/F12 containing 0.1% BSA). The cells were treated with the test compound for 5 min and then given AVP (1 nM) in assay media containing 1 mM isobutylmethylxanthine. After 5 min, 0.5 N HCl was added to disrupt the cells and solubilize cAMP. The cAMP content of 20 μL of the cell lysate in each well was measured using cAMP Flashplates (NEN Life Sciences). Data are expressed as pmol cAMP/well. While the assay is optimized to detect and quantitate antagonistic activity, agonistic activity would also be apparent at the higher concentrations of test compounds.

Intracellular calcium mobilization was measured in HEK-293 cells transfected to express either human V1a, oxytocin or V1b receptors. Cells were plated into black 96-well Packard Clear-View plates 4 to 7 d prior to use. The cells were loaded with fluo-3 AM (Molecular Probes, Inc., Eugene, Oreg.) in buffer (25 mM Hepes, 125 mM NaCl, 1 g/L glucose, 0.1% BSA, 5 mM KCl, 0.5 mM $CaCl_2$, 0.5 mM $MgCl_2$, pH 7.45) containing Pluronic (Molecular Probes). Cells were incubated with 5 μM fluo-3 AM for 1 h shielded from light at room temperature. Intracellular fluorescence was measured using FLIPR (fluorometric imaging plate reader; Molecular Devices, Inc., Sunnyvale, Calif.). The FLIPR protocol called for images to be collected at one second intervals with 50 μL of the test compound added after the initial 10 images. An additional 70 images were then taken to detect any compound agonistic activity. FLIPR then added 50 μL of agonist peptide and collected a final 40 images for quantitating compound antagonistic activity. V1a- and V1b-expressing HEK cells were challenged with 1 nM and 0.5 nM AVP, respectively. Oxytocin-expressing HEK cells were challenged with 0.5 nM oxytocin (Peninsula Labs).

The data from the cAMP accumulation and the calcium mobilization assays are expressed as IC50 values as determined from dose response curves.

TABLE I

| | In Vitro Results | | |
| | Binding | Functional | |
| Cpd | V1a (% inhib @ 0.2 μM) | V2 (IC$_{50}$; μM) | V2 (IC$_{50}$; μM) |
|---|---|---|---|
| 1 | 1% | 0.500 | — |
| 2 | 0% | 0.240 | 0.280 |
| 3 | 0% | 0.340 | 0.710 |
| 4 | 0% | 22% @ 0.2 μM | >10 |
| 5 | 0% | 0.160 | 0.775 |
| 6 | 0% | 0.066 | 0.025 |
| 7 | 4% | 0.050 | 0.02 |
| 8 | 0% | 0.400 | 1.08 |
| 9 | 2% | 0.045 | 0.040 |
| 10 | 2% | 0.065 | 0.030 |
| 11 | 0% | 0.230 | 0.773 |
| 12 | 6% | 0.028 | 0.020 |

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

All publications disclosed in the above specification are hereby incorporated by reference in full.

What is claimed is:

1. A compound of Formula (I):

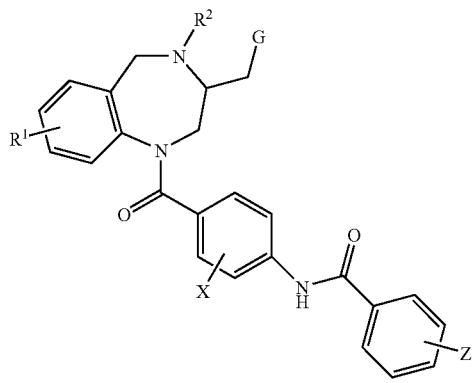

Formula (I)

wherein:
R$^1$ is independently selected from the group consisting of hydrogen, C$_{1-6}$alkyl, C$_{1-6}$alkoxy, and one to three halogen atoms;
R$^2$ is independently selected from the group consisting of hydrogen, C$_{1-6}$alkyl, aryl(C$_{1-6}$)alkyl, cycloalkyl(C$_{1-6}$)alkyl, (C$_{1-6}$)alkylsulfonyl, arylsulfonyl, and C$_{1-6}$alkylcarbonyl;
G is independently selected from the group consisting of C$_{1-8}$alkyl, C$_{1-8}$alkoxy, C$_{3-10}$cycloalkoxy, C$_{1-8}$alkylcarbonyloxy, hydroxy, heterocyclyl, C$_{1-6}$alkylthio, C$_{1-6}$alkylsulfonyloxy, arylsulfonyloxy, and NR$^a$R$^b$;
R$^a$ and R$^b$ are independently selected from the group consisting of hydrogen and C$_{1-6}$alkyl; or, R$^a$ and R$^b$ are taken with the nitrogen atom to which they are both attached form a 3 to 7 membered monocyclic heterocycle;
provided that when R$^2$ is hydrogen or C$_{1-6}$alkyl, G is other than C$_{1-8}$alkyl, C$_{1-8}$alkoxy, hydroxy, C$_{1-6}$alkylsulfonyloxy, C$_{1-8}$alkylcarbonyloxy, or NR$^a$R$^b$; such that R$^a$ and R$^b$ are not taken together to form a heterocycle;
X is independently selected from the group consisting of hydrogen, C$_{1-6}$alkyl, C$_{1-6}$alkoxy, and halogen;
Z is one to three substituents independently selected from the group consisting of C$_{1-6}$alkyl, C$_{1-6}$alkoxy, C$_{1-6}$alkylthio, halogen, hydroxy, nitro, and aryl, wherein said aryl is optionally substituted with one to five substituents independently selected from the group consisting of C$_{1-6}$alkyl, C$_{1-6}$alkoxy, hydroxy, C$_{1-6}$alkylthio, and halogen; and wherein the C$_{1-6}$alkyl and C$_{1-6}$alkoxy substituents of Z are optionally fluorinated with one to thirteen fluorine atoms;
and pharmaceutically acceptable enantiomers, diastereomers, racemates, and salts thereof.

2. The compound according to claim 1 wherein R$^1$ is independently selected from the group consisting of hydrogen, C$_{1-6}$alkyl, and one to two halogen atoms.

3. The compound according to claim 2 wherein R$^1$ is independently selected from the group consisting of hydrogen, C$_{1-3}$alkyl, and one to two halogen atoms selected from the group consisting of chlorine and fluorine.

4. The compound according to claim 3 wherein R$^1$ is independently selected from the group consisting of hydrogen, methyl, chlorine, and fluorine.

5. The compound according to claim 1 wherein R$^2$ is independently selected from the group consisting of hydrogen, C$_{1-3}$alkyl, aryl(C$_{1-3}$)alkyl, (C$_{1-3}$)alkylsulfonyl, arylsulfonyl, and C$_{1-3}$alkylcarbonyl; provided that when R$^2$ is hydrogen or C$_{1-3}$alkyl, G is a substituent other than C$_{1-8}$alkyl, C$_{1-8}$alkoxy, hydroxy, C$_{1-6}$alkylsulfonyloxy, C$_{1-8}$alkylcarbonyloxy, or NR$^a$R$^b$; such that R$^a$ and R$^b$ are not taken together to form a heterocycle.

6. The compound according to claim 5 wherein R$^2$ is independently selected from the group consisting of hydrogen, methyl, propyl, methanesulfonyl, propanesulfonyl, benzenesulfonyl, and C$_{1-3}$alkylcarbonyl; provided that when R$^2$ is hydrogen, methyl, or propyl, G is a substituent other than C$_{1-8}$alkyl, C$_{1-8}$alkoxy, hydroxy, C$_{1-6}$alkylsulfonyloxy, C$_{1-8}$alkylcarbonyloxy, or NR$^a$R$^b$; such that R$^a$ and R$^b$ are not taken together to form a heterocycle.

7. The compound according to claim 6 wherein R$^2$ is independently selected from the group consisting of hydrogen, methyl, methanesulfonyl, and methylcarbonyl; provided that when R$^2$ is hydrogen or methyl, G is a substituent other than C$_{1-8}$alkyl, C$_{1-8}$alkoxy, hydroxy, C$_{1-6}$alkylsulfonyloxy, C$_{1-8}$alkylcarbonyloxy, or NR$^a$R$^b$; such that R$^a$ and R$^b$ are not taken together to form a heterocycle.

8. The compound according to claim 1 wherein G is independently selected from the group consisting of C$_{1-3}$alkyl, C$_{1-3}$alkoxy, C$_{3-8}$cycloalkoxy, C$_{1-3}$alkylcarbonyloxy, hydroxy, heterocyclyl, C$_{1-3}$alkylthio, C$_{1-3}$alkylsulfonyloxy, arylsulfonyloxy and NR$^a$R$^b$; provided that when R$^2$ is hydrogen or C$_{1-6}$alkyl, G is other than C$_{1-3}$alkyl, C$_{1-3}$alkoxy, hydroxy, C$_{1-3}$alkylcarbonyloxy, C$_{1-3}$alkylsulfonyloxy, or NR$^a$R$^b$; such that R$^a$ and R$^b$ are not taken together to form a heterocycle.

9. The compound according to claim 8 wherein G is independently selected from the group consisting of C$_{1-3}$alkyl, C$_{1-3}$alkoxy, C$_{1-3}$alkylcarbonyloxy, hydroxy, heterocyclyl, C$_{1-3}$alkylthio, C$_{1-3}$alkylsulfonyloxy, arylsulfonyloxy, and NR$^a$R$^b$; provided that when R$^2$ is hydrogen or C$_{1-6}$alkyl, G is other than C$_{1-3}$alkyl, C$_{1-3}$alkoxy, hydroxy, C$_{1-3}$alkylcarbonyloxy, C$_{1-3}$alkylsulfonyloxy, or NR$^a$R$^b$; such that R$^a$ and R$^b$ are not taken together to form a heterocycle.

10. The compound according to claim 9 wherein G is independently selected from the group consisting of methoxy, methylcarbonyloxy, hydroxy, morpholino, methylthio, methanesulfonyloxy, benzenesulfonyloxy, and NR$^a$R$^b$; provided that when R$^2$ is hydrogen or C$_{1-6}$alkyl, G is other than methoxy, hydroxy, methylcarbonyloxy, methanesulfonyloxy, or NR$^a$R$^b$; such that R$^a$ and R$^b$ are not taken together to form a heterocycle.

11. The compound according to claim 10 wherein G is independently selected from the group consisting of methoxy, methylcarbonyloxy, hydroxy, morpholino, methylthio, benzenesulfonyloxy, dimethylamino, and pyrrolidin-1-yl; provided that when R$^2$ is hydrogen or C$_{1-6}$alkyl, G is other than methoxy, hydroxy, methylcarbonyloxy, or dimethylamino.

12. The compound according to claim 11 wherein G is methoxy or hydroxy when R$^2$ is other than hydrogen or C$_{1-6}$alkyl.

13. The compound according to claim 1 wherein R$^a$ and R$^b$ are independently selected from the group consisting of hydrogen and C$_{1-3}$alkyl; or R$^a$ and R$^b$ are taken together with the nitrogen atom to which they are both attached to form a 3 to 7 membered monocyclic heterocycle.

14. The compound according to claim 1 wherein X is independently selected from the group consisting of hydrogen, C$_{1-3}$alkyl, C$_{1-3}$alkoxy, and halogen.

15. The compound according to claim 14 wherein X is independently selected from the group consisting of hydrogen, methyl, methoxy, chlorine, and fluorine.

16. The compound according to claim 15 wherein X is independently selected from the group consisting of hydrogen, methoxy, and chlorine.

17. The compound according to claim 1 wherein Z is one to three substituents independently selected from the group consisting of C$_{1-3}$alkyl, C$_{1-3}$alkoxy, C$_{1-3}$alkylthio, halogen, hydroxy, nitro, and aryl, wherein said aryl is optionally substituted with one to five substituents independently selected from the group consisting of C$_{1-3}$alkyl, C$_{1-3}$alkoxy, hydroxy, C$_{1-3}$alkylthio, and halogen; and wherein the C$_{1-3}$alkyl and C$_{1-3}$alkoxy substituents of Z are optionally fluorinated with one to seven fluorine atoms.

18. The compound according to claim 17 wherein Z is one to two substituents independently selected from the group consisting of methyl, methoxy, methylthio, fluorine, chlorine, hydroxy, nitro, and phenyl, wherein said phenyl is optionally substituted with one to five substituents independently selected from the group consisting of methyl, methoxy, hydroxy, methylthio, fluorine, and chlorine; and wherein the methyl and methoxy substituents of Z are optionally fluorinated with one to three fluorine atoms.

19. The compound according to claim 18 wherein Z is one to two substituents independently selected from the group consisting of methyl, fluorine, chlorine, and phenyl, wherein said phenyl is optionally substituted with one to three substituents independently selected from the group consisting of methyl, methoxy, hydroxy, fluorine, and chlorine; and wherein the methyl substituents of Z are optionally fluorinated with one to three fluorine atoms.

20. The compound according to claim 19 wherein Z is a phenyl ring positioned ortho to the aminocarbonyl of Formula (I) and optionally an additional substituent selected from the group consisting of methyl, fluorine, and chlorine; wherein said phenyl is optionally substituted with one to three substituents independently selected from the group consisting of methyl, methoxy, hydroxy, fluorine, and chlorine.

21. A compound of Formula (Ia):

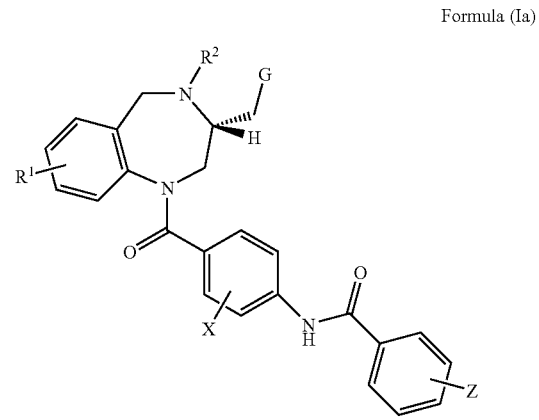

Formula (Ia)

wherein:

R$^1$ is independently selected from the group consisting of hydrogen, C$_{1-6}$alkyl, and one to two halogen atoms;

R$^2$ is independently selected from the group consisting of hydrogen, C$_{1-3}$alkyl, aryl(C$_{1-3}$)alkyl, (C$_{1-3}$)alkylsulfonyl, arylsulfonyl, and C$_{1-6}$alkylcarbonyl;

G is independently selected from the group consisting of methoxy, methylcarbonyloxy, hydroxy, morpholino, methylthio, methanesulfonyloxy, benzenesulfonyloxy, and NR$^a$R$^b$;

wherein R$^a$ and R$^b$ are independently selected from the group consisting of hydrogen and C$_{1-3}$alkyl; or, R$^a$ and R$^b$ are taken with the nitrogen atom to which they are both attached to form a 3 to 7 membered monocyclic heterocycle;

provided that when R$^2$ is hydrogen or C$_{1-3}$alkyl, G is other than methoxy, hydroxy, methylcarbonyloxy, methanesulfonyloxy, or NR$^a$R$^b$; such that R$^a$ and R$^b$ are not taken together to form a heterocycle;

X is independently selected from the group consisting of hydrogen, C$_{1-3}$alkyl, C$_{1-3}$alkoxy, and halogen;

Z is one to two substituents independently selected from the group consisting of methyl, methoxy, methylthio, fluorine, chlorine, hydroxy, nitro, and phenyl, wherein said phenyl is optionally substituted with one to five substituents independently selected from the group consisting of methyl, methoxy, hydroxy, methylthio, fluorine, and chlorine; and wherein the methyl and methoxy substituents of Z are optionally fluorinated with one to three fluorine atoms;

and pharmaceutically acceptable enantiomers, diastereomers, racemates, and salts thereof.

22. The compound according to claim 21 wherein R$^2$ is independently selected from the group consisting of aryl (C$_{1-3}$)alkyl, (C$_{1-3}$)alkylsulfonyl, arylsulfonyl, and C$_{1-6}$alkylcarbonyl; and G is independently selected from the group consisting of methoxy and hydroxy.

23. A compound of Formula (Ia):

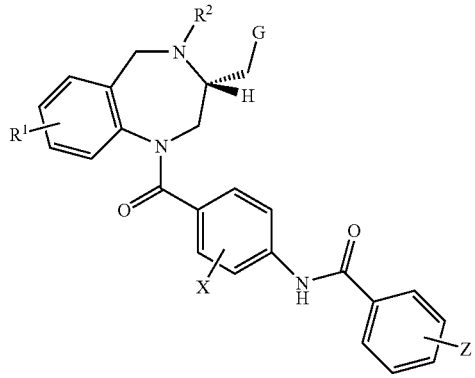

Formula (Ia)

wherein:
R¹ is independently selected from the group consisting of hydrogen, $C_{1-3}$alkyl, and one to two chlorine or fluorine atoms;
R² is independently selected from the group consisting of hydrogen, methyl, propyl, methanesulfonyl, propanesulfonyl, benzenesulfonyl, and $C_{1-3}$alkylcarbonyl;
G is independently selected from the group consisting of methoxy, methylcarbonyloxy, hydroxy, morpholino, methylthio, benzenesulfonyloxy, dimethylamino, and pyrrolidin-1-yl; provided that when R² is hydrogen, methyl or propyl, G is other than methoxy, hydroxy, methylcarbonyloxy, or dimethylamino;
X is independently selected from the group consisting of hydrogen, methyl, methoxy, chlorine, and fluorine;
Z is one to two substituents independently selected from the group consisting of methyl, fluorine, chlorine, and phenyl; wherein said phenyl is optionally substituted with one to three substituents independently selected from the group consisting of methyl, methoxy, hydroxy, fluorine, and chlorine; and wherein the methyl substituents of Z are optionally fluorinated with one to three fluorine atoms;
and pharmaceutically acceptable enantiomers, diastereomers, racemates, and salts thereof.

24. The compound according to claim 23 wherein Z is one to two substituents independently selected from the group consisting of methyl, fluorine, chlorine, and phenyl.

25. The compound according to claim 24 wherein at least one Z is phenyl or methyl and positioned ortho to the aminocarbonyl of Formula (Ia).

26. The compound according to claim 25 wherein Z is phenyl and positioned ortho to the aminocarbonyl of Formula (Ia).

27. The compound according to claim 23 wherein:
R¹ is independently selected from the group consisting of hydrogen, methyl, chlorine, and fluorine;
R² is independently selected from the group consisting of hydrogen, methyl, methanesulfonyl, and methylcarbonyl;
G is independently selected from the group consisting of methoxy, methylcarbonyloxy, hydroxy, morpholino, methylthio, benzenesulfonyloxy, dimethylamino, and pyrrolidin-1-yl; provided that when R² is hydrogen or methyl, G is other than methoxy, hydroxy, methylcarbonyloxy, or dimethylamino;
X is independently selected from the group consisting of hydrogen, methoxy, and chlorine.

28. The compound according to claim 27 wherein Z is phenyl and positioned ortho to the aminocarbonyl of Formula (Ia).

29. A compound of Formula (Ib):

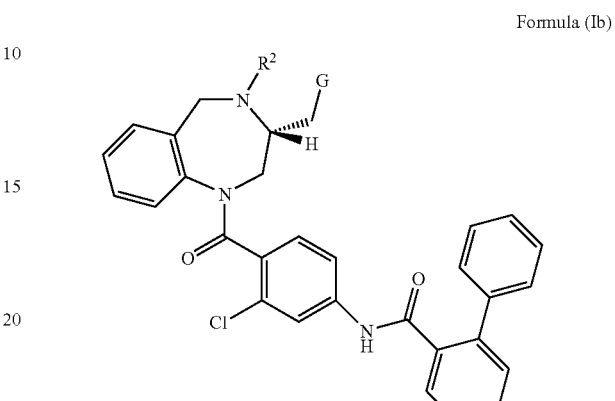

Formula (Ib)

selected from the group consisting of:
a compound of Formula (Ib) wherein R² $CH_2Ph$ and G is OH;
a compound of Formula (Ib) wherein R² is $CH_3$ and G is $SCH_3$;
a compound of Formula (Ib) wherein R² is $CH_3$ and G is

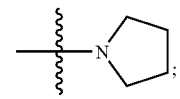

;

a compound of Formula (Ib) wherein R² is $CH_3$ and G is

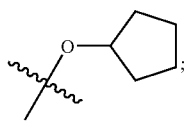

;

a compound of Formula (Ib) wherein R² is $CH_3$ and G is

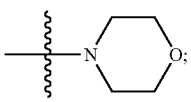

;

a compound of Formula (Ib) wherein R² is $SO_2CH_3$ and G is OH;
a compound of Formula (Ib) wherein R² is $SO_2CH_3$ and G is $OSO_2CH_3$;
a compound of Formula (Ib) wherein R² is $C(=O)CH_3$ and G is $OC(=O)CH_3$;
a compound of Formula (Ib) wherein R² is $SO_2(CH_2)_2CH_3$ and G is OH;
a compound of Formula (Ib) wherein R² is $SO_2Ph$ and G is OH; and
a compound of Formula (Ib) wherein R² is $C(=O)CH_3$ and G is OH.

30. A pharmaceutical composition comprising a pharmaceutically acceptable carrier and a compound of claim 1.

31. A pharmaceutical composition made by mixing a compound of claim 1 and a pharmaceutically acceptable carrier.

32. A method of treatment comprising administering to a subject having a condition selected from the group consisting of hypertension, congestive heart failure, cardiac insufficiency, coronary vasospasm, cardiac ischemia, liver cirrhosis, renal vasospasm, renal failure, cerebral edema and ischemia, stroke, thrombosis, and water retention a therapeutically effective amount of the compound of claim 1.

33. The method of claim 32, wherein the condition is congestive heart failure.

34. The method of claim 33, wherein the therapeutically effective amount of the compound is about 0.1 to about 300 mg/kg/day.

35. A method of treatment comprising administering to a subject with a condition selected from the group consisting of hypertension, congestive heart failure, cardiac insufficiency, coronary vasospasm, cardiac ischemia, liver cirrhosis, renal vasospasm, renal failure, cerebral edema and ischemia, stroke, thrombosis, and water retention a therapeutically effective amount of the composition of claim 26.

36. The method of claim 35, wherein the condition is congestive heart failure.

37. The method of claim 35, wherein the therapeutically effective amount of the compound is about 0.1 to about 300 mg/kg/day.

38. A method of treatment comprising administering to a subject with a condition selected from the group consisting of hypertension, congestive heart failure, cardiac insufficiency, coronary vasospasm, cardiac ischemia, liver cirrhosis, renal vasospasm, renal failure, cerebral edema and ischemia, stroke, thrombosis, or water retention a therapeutically effective amount of the composition of claim 29.

39. The method of claim 38, wherein the condition is congestive heart failure.

40. The method of claim 38, wherein the therapeutically effective amount of the compound is about 0.1 to about 300 mg/kg/day.

\* \* \* \* \*